US011135449B2

(12) United States Patent
Johnson et al.

(10) Patent No.: US 11,135,449 B2
(45) Date of Patent: Oct. 5, 2021

(54) MACHINE VISION ALIGNMENT AND POSITIONING SYSTEM FOR ELECTRON BEAM TREATMENT SYSTEMS

(71) Applicant: INTRAOP MEDICAL CORPORATION, Sunnyvale, CA (US)

(72) Inventors: Richard L. Johnson, Suffolk, VA (US); Christopher J. Patane, San Mateo, CA (US); David H. Whittum, Sunnyvale, CA (US)

(73) Assignee: INTRAOP MEDICAL CORPORATION, Sunnyvale, CA (US)

( * ) Notice: Subject to any disclaimer, the term of this patent is extended or adjusted under 35 U.S.C. 154(b) by 0 days.

(21) Appl. No.: 16/609,966

(22) PCT Filed: May 3, 2018

(86) PCT No.: PCT/US2018/030897
§ 371 (c)(1),
(2) Date: Oct. 31, 2019

(87) PCT Pub. No.: WO2018/204649
PCT Pub. Date: Nov. 8, 2018

(65) Prior Publication Data
US 2020/0054896 A1    Feb. 20, 2020

Related U.S. Application Data

(60) Provisional application No. 62/501,377, filed on May 4, 2017.

(51) Int. Cl.
*A61N 5/10* (2006.01)

(52) U.S. Cl.
CPC ........... *A61N 5/1065* (2013.01); *A61N 5/103* (2013.01); *A61N 5/1049* (2013.01); *A61N 2005/105* (2013.01); *A61N 2005/1089* (2013.01)

(58) Field of Classification Search
None
See application file for complete search history.

(56) References Cited

U.S. PATENT DOCUMENTS

| 3,201,065 A | 8/1965 | Dunn |
| 3,391,881 A | 7/1968 | Maltby |
| (Continued) | | |

FOREIGN PATENT DOCUMENTS

| WO | 2014/116868 A1 | 7/2014 |
| WO | 2017/151763 A1 | 9/2017 |

OTHER PUBLICATIONS

PCT/US2018/030897, International Search Report, dated Sep. 6, 2018, pp. 1-4.

(Continued)

*Primary Examiner* — Hoon K Song
(74) *Attorney, Agent, or Firm* — Kagan Binder PLLC

(57) ABSTRACT

The present invention provides improved methods and apparatus that use machine vision techniques to rapidly and automatically guide objects into desired docking configurations. The present invention is based at least in part upon using multi-depth, rotationally symmetric targets that are observed from two or more observation perspectives. By taking advantage of parallax effects associated with the multi-depth topography of the target, the apparent positions of target features in captured image information encodes position and angular alignment of the objects relative to each other in three dimensional space. The practice of the present invention provides a fast, accurate, reliable and automatic approach to achieve hard or soft docking configurations in the electron beam therapies as well as to implement real-time gating and tracking during the course of a treatment.

25 Claims, 14 Drawing Sheets

(56) References Cited

U.S. PATENT DOCUMENTS

| | | | |
|---|---|---|---|
| 3,820,035 A | | 6/1974 | Meddaugh |
| 4,638,814 A | * | 1/1987 | Spanswick ............ A61N 5/1049 607/154 |
| 4,891,767 A | | 1/1990 | Rzasa et al. |
| 4,995,087 A | | 2/1991 | Rathi et al. |
| 5,321,271 A | | 6/1994 | Schonberg et al. |
| 5,418,372 A | | 5/1995 | Schonberg et al. |
| 5,661,377 A | | 8/1997 | Mishin et al. |
| 5,745,545 A | * | 4/1998 | Hughes .................... A61B 6/08 378/206 |
| 5,993,523 A | | 8/1999 | Drisko et al. |
| 6,076,005 A | | 6/2000 | Sontag et al. |
| 6,078,036 A | * | 6/2000 | Cook .................... A61N 5/1049 250/206.1 |
| 6,118,847 A | | 9/2000 | Hernandez-Guerra et al. |
| 6,137,893 A | | 10/2000 | Michael et al. |
| 6,346,966 B1 | | 2/2002 | Toh |
| 6,362,875 B1 | | 3/2002 | Burkley |
| 6,554,452 B1 | * | 4/2003 | Bourn ................ G01N 21/8806 313/113 |
| 6,690,965 B1 | | 2/2004 | Riaziat et al. |
| 6,871,993 B2 | | 3/2005 | Hecht |
| 7,894,649 B2 | | 2/2011 | Fu et al. |
| 8,111,025 B2 | | 2/2012 | Whittum et al. |
| 8,269,197 B2 | | 9/2012 | Goer et al. |
| 9,393,439 B2 | | 7/2016 | Goer |
| 2009/0126760 A1 | | 5/2009 | Banerjee et al. |
| 2010/0166294 A1 | | 7/2010 | Marrion et al. |
| 2019/0314645 A1 | * | 10/2019 | Ciresianu ............ A61N 5/1082 |

OTHER PUBLICATIONS

Keane, MD, et al., "Intraoperative Radiotherapy in the Era of Intensive Neoadjuvant Chemotherapy and Chemoradiotherapy for Pancreatic Adenocarcinoma" American Journal of Clinical Oncology, vol. 00, No. 00 (2016), pp. 1-6.

Balter et al., "Anniversary Paper: A sampling of novel technologies and the role of medical physicists in radiation oncology" Med. Phys. 35 (12), Dec. 2008, pp. 5641-5652.

Casali et al, "An electron beam imaging system for quality assurance in IORT" Nucl. Instr. and Meth. in Phys. Res. B 213 (2004) pp. 616-620.

Palta, Ph.D., et al., "Intraoperative Electron Beam Radiation Therapy: Technique, Dosimetry, and Dose Specification: Report Task of Force 48 of the Radiation Therapy Committee, American Associate of Physicists in Medicine" Int. J. Radiation Oncology Biol. Phys., vol. 33, No. 3, (1995) pp. 725-745.

Radiation Products Design, Inc., Periscopic Viewer, May 27, 2017, pp. 1-4.

Beddar et al., "Intraoperative radiation therapy using mobile electron linear accelerators: Report of AAPM Radiation Therapy Committee Task Group No. 72" Med. Phys. 33, (2006) pp. 1476-1489.

Whittum, "Microwave Electron Linacs for Oncology", Reviews of Accelerator Science and Technology, vol. 2 (2009) pp. 63-92.

Willett et al, Intraoperative Radiation Therapy: Journal of Clinical Oncology, vol. 25, No. 8, (2007) pp. 971-977.

R.M. Wilenzick, Department of Radiation Therapy, Alton Ochsner Medical Foundation, W.S. Kubricht, Jr., et al, Mary Bird Perkins Radiatio Treatment Center, "Evaluation of a Commercial Applicator System for Intraoperative Radiotherapy" (1985) pp. 1-20.

K.R. Hogstrom, et al., "Design of metallic electron beam cones for an intraoperative therapy linear accelerator" Int. J. Radiat. Oncol. Biol. Phys. 18, (1990) pp. 1223-1232.

J. R. Palta and N. Suntharalingam, "A nondocking intraoperative electron beam applicator system" Int. J. Radiat. Oncol. Biol. Phys. 17, (1989) pp. 411-417.

C. E. Nelson, et al., "The dosimetry properties of an intraoperative radiation therapy applicator system for a Mevatron-80" Med. Phys. 16, (1989) pp. 794-799.

C.J. Karzmark, et al., Medical Electron Accelerators (McGraw-Hill, New York, 1993), Chapter 8, Treatment Beam Production, pp. 137-156 (cover pages and contents pp. v-xii).

C.J. Karzmark, et al., Medical Electron Accelerators (McGraw-Hill, New York, 1993), Chapter 11, Multi-X-Ray Energy Accelerators, pp. 189-199 (cover pages and contents pp. v-xii).

McCullough, et al., Technical Notes "The dosimetric properties of an applicator system for intraoperative electron-beam therapy utilizing a Clinac-18 accelerator" Med. Phys. vol. 9, No. 2 (21, Mar./Apr. 1982) pp. 261-268.

H. Kharrati, et al., "Design of a non-docking intraoperative electron beam applicator system" Radiotherapy and Oncology 33(1) (1994) pp. 80-83.

K.J. Day, B.A., et al., "The 4 MeV Linear Accelerator At Newcastle Upon Tyne" Brit. J. Radiol. 31 (1958) pp. 669-682.

M. Weissbluth, et al., The Stanford Linear Accelerator "II. Installation and Physical Measurements" Radiology, 72 (2) (1959) pp. 242-253.

Thwaites et al., "Back to the future: the history and development of the clinical linear accelerator", Phys. Med. Biol. 51 (2006) R343-R362.

Jones, "Apparatus, Technique and Dosimetry of Intraoperative Electron Beam Therapy" Vaeth JM, Meyer JL (eds): The Role of High Energy Electrons in the Treatment of Cancer. 25th Annual San Francisco Cancer Symposium, Feb. 1990. Front Radiat Ther Oncol. Basel, Karger, vol. 25 (1991) pp. 233-245.

Rahman, et al., "Electron FLASH Delivery at Treatment Room Isocenter for Efficient Reversible Conversion of a Clinical LINAC", International Journal of Radiation Oncology, Biology, Physics, (2021), manuscript pp. 1-21, supplemental pp. 1-2, appendix pp. 1-2.

Esplen et al., Physics and biology of ultrahigh dose-rate (FLASH) radiotherapy: a topical review Institute of Physics and Engineering in Medicine, vol. 65, No. 23 (2020) pp. 1-107.

* cited by examiner

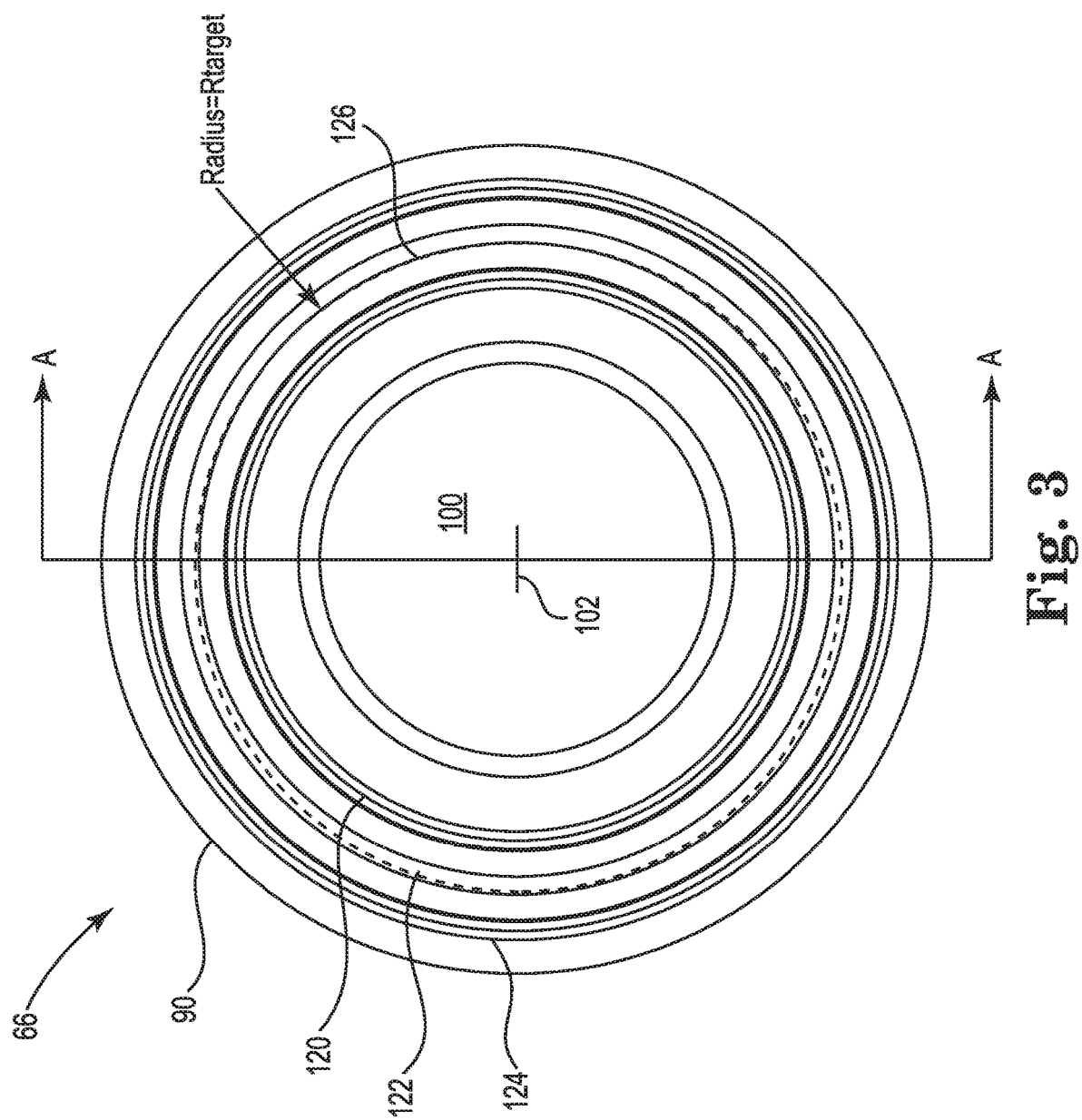

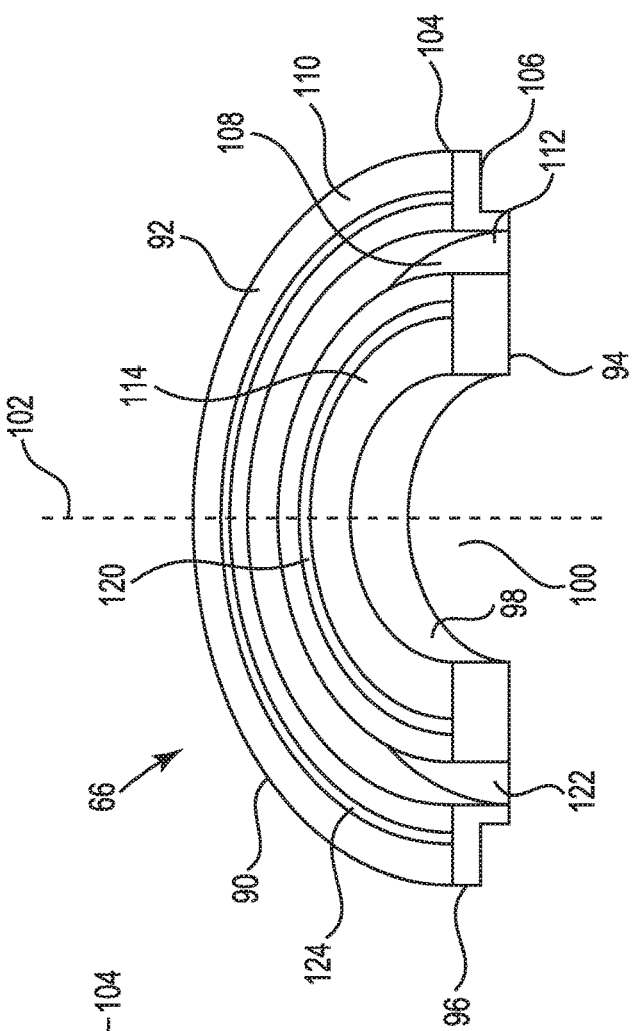
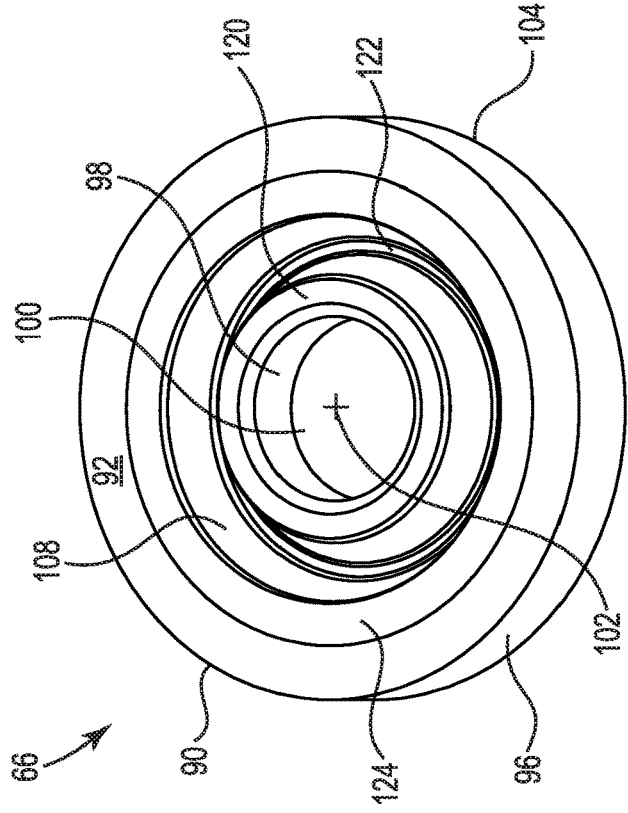

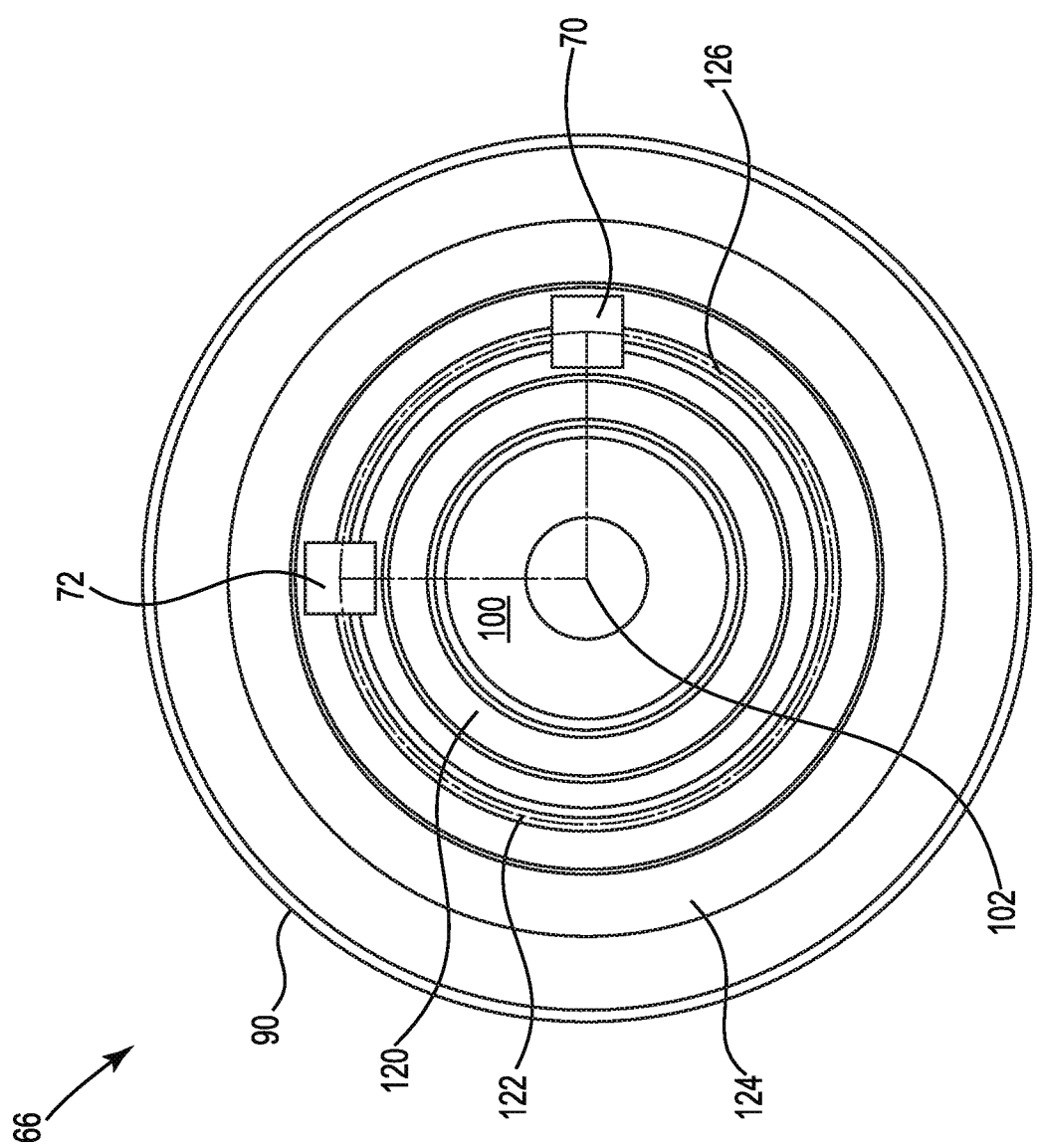

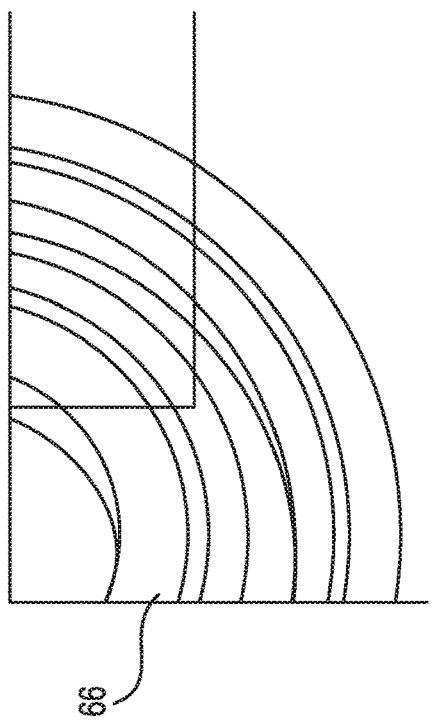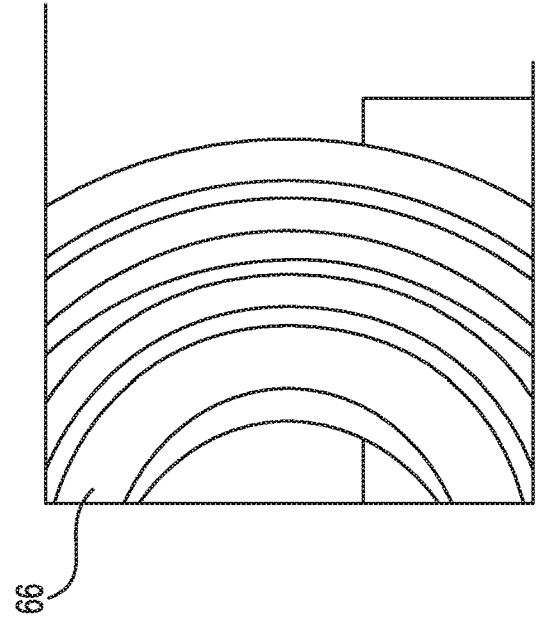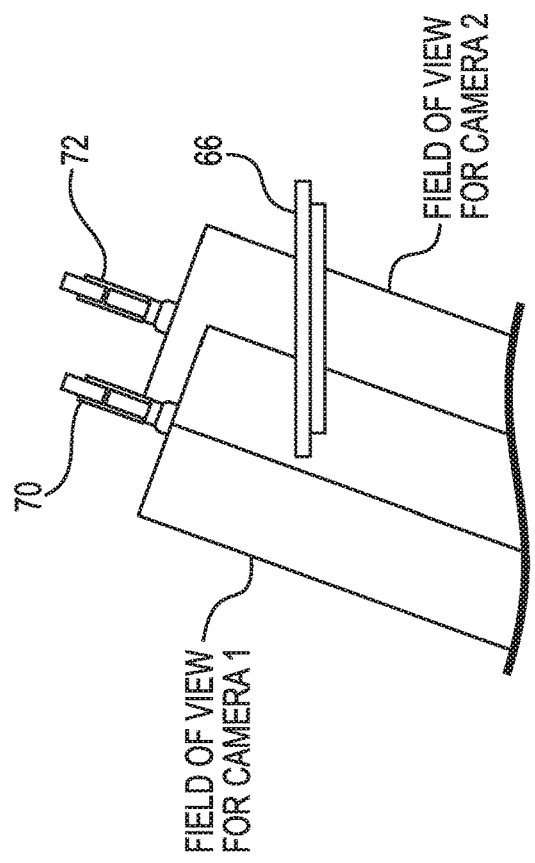

MACHINE VISION ALIGNMENT AND POSITIONING SYSTEM FOR ELECTRON BEAM TREATMENT SYSTEMS

PRIORITY CLAIM

This application claims priority to International Application No. PCT/US2018/030897, filed on May 3, 2018, which in turn claims priority under 35 USC 119 to U.S. Provisional Patent Application No. 62/501,377, filed May 4, 2017, the entireties of which are respectively incorporated herein by reference for all purposes.

FIELD OF THE INVENTION

The present invention relates to the field of using machine vision to align and position an electron beam treatment system relative to a treatment site in order to carry out electron beam therapy. More particularly, the present invention relates to using machine vision to observe a multi-dimensional target in which the apparent position of image features in captured image information encodes position and angular alignment information.

BACKGROUND OF THE INVENTION

Megavoltage beams have long been used for the treatment of cancer, dermatological conditions and for cosmesis, for or as an adjunct to surgery, or, without surgery. Applications to treatment of cancer include the prevention of recurrence, delay of recurrence, and palliative treatment. Intraoperative radiation therapy is also effective in extending life, even in the case of unresectable tumors. F. K. Keane, et al., Am. J. Clin. Oncology, October 2016. Other applications in treating cancer include treatment of mycosis fungoides and basal cell carcinoma, and less typically melanoma or desmoplastic melanoma. Radiation also may be used to treat dermatological conditions and/or to provide cosmesis.

Exemplary applications in the dermatological field include prevention or treatment of scarring of the dermis including hypertrophic scarring, dermal fibroproliferative lesions, and benign fibrous tumors such as keloids, which as is known can reach 1 cm above the skin surface. In some embodiments, electron beam radiation may be used to treat or prevent scar formation resulting from breast cancer surgical procedures or reduce the severity of scar formation in emergency room procedures. Other exemplary applications include treatment for internal conditions such as surgical adhesions and restenosis, as may occur when a blood vessel is treated for blockage. For example, a common problem with abdominal surgery is that the surgery itself creates scarring which can result in tissue adhesions or organ adhesions. Typically these do not interfere with normal functioning, but they make re-surgery to the same site more difficult. An electron beam treatment may be used to irradiate the microvasculature of the surgical bed to reduce the probability of formation of surgical adhesions. As another example, as an adjunct to vascular surgery, a treatment may be used to treat the anastomosis of blood vessels such as the femoral artery, popliteal artery and carotid artery to help prevent restenosis.

Early intraoperative radiation treatment methods used X-rays as a radiation source. More recent intraoperative therapy installations have used electron beams as a radiation source. Advantageously, electron beam radiation provides a homogeneous dose of radiation with a rapid falloff in radiation intensity beyond the treatment volume, thereby minimizing exposure of noncancerous tissue to the radiation.

Prior art in the area of radiation therapy is extensive, including proton, ion, photon and electron radiotherapy, kilovoltage therapy and brachytherapy. Waldemar Scharf *Biomedical Particle Accelerators*, (AIP, New York, 1993) ISBN-13: 000-156396-089-3. Each of these approaches offers differences in depth-dose characteristic, mode of delivery, and patient experience. Other differences include applicability to different indications, outcomes and cost. Prior art specific to electron accelerators covers many embodiments, both with respect to mechanical actuation, the underlying accelerator technology and beam shaping devices.

Mechanical implementations are numerous (S. Baiter and J. M. Bailter, "Anniversary Paper: A Sampling of novel technologies and the role of medical physicists in radiation oncology", Med. Phys. 35 (12), December 2008) and have included a fixed linac (M J. Day and F. T. Farmer, "The 4 MeV Linear Accelerator at Newcastle Upon Tyne", Brit J. Radiol. 31 (1958) pp. 669-682), a trunnion hung from a crane ("The Stanford Linear Accelerator", M. Weissbluth, et al., Radiology, 72 (2) (1959)), a double-gantry system (D. I. Thwaites and J. B. Tuohy, "Back to the future: the history and development of the clinical linear accelerator", Phys. Med. Biol. 51, 2006), a C-arm gantry (C. J. Karzmark, Craig S. Nunan and Eiji Tanabe, *Medical Electron Accelerators* (McGraw-Hill, New York, 1993), a robotic arm (G. Kurup, CyberKnife: A new paradigm in radiotherapy, J Med Phys. 2010 April-June; 35(2): 63-64), and a ring-gantry ("CT") mounting (T. Rock Mackie, Timothy Holmes, Stuart Swerdlofl Paul Reckwerdt, Joseph O. Deasy, James Yang, Bhudatt Paliwal, and Timothy Kinsella, "Tomotherapy: A new concept for the delivery of dynamic conformal radiotherapy", Med. Phys. 20 (1993) pp. 1709-1719). A configuration of great interest for intraoperative radiation therapy (IORT) is the Mobetron electron beam machine (A. Sam Beddar, et al., "Intraoperative radiation therapy using mobile electron linear accelerators: Report of AAPM Radiation Therapy Committee Task Group No. 72", Med. Phys. 33 (5) 2006). The self-shielded Mobetron machine incorporates five independently driven degrees of freedom, with motion in the horizontal plane unlimited, including transport down standard hallways and in elevators. Other accelerator system configurations are found in the references.

Therapeutic radiation is designed to penetrate deeply as most targets for therapeutic radiation are located well below the surface. To allow unaffected (normal) tissue to recover, the therapeutic radiation is generally delivered in many daily treatments, called fractions, relying on the principle that well-oxygenated normal tissues will repair and recover from radiation damage more quickly than the tissues being targeted by the therapeutic radiation. Even when the therapeutic radiation is delivered in fractions, permanent radiation damage to healthy tissues surrounding the radiation site may still occur.

It is therefore desirable to provide a radiation device that deposits a substantial portion of its radiation at the target tissues and much less radiation to the normal tissues surrounding the target. This is especially challenging for targets that are at or close to the surface since therapeutic radiation devices are designed to penetrate deeply. Electron beams are ideal for depositing radiation more or less uniformly through a volume of finite, well-defined depth, where depth of dose depends on beam energy, typically 6 MeV (20 mm), 9 MeV (30 mm), 12 MeV (40 mm).

It is desirable too that the radiation may be delivered intraoperatively (IORT) as this permits sparing of the healthy tissue of the epidermis where appropriate, and enables escalation of the single-treatment dose to 20 Gy. In this way, the treatment may be administered in the short period of time in which the patient is in the operating room. The MOBETRON-branded electron beam machines available from IntraOp Medical Corporation advantageously is capable of delivering 10 Gy/min, and thus a 20 Gy treatment in 2 min. However, the time required for docking represents additional time during which the patient is in surgery, when time may be of the essence.

In a representative intraoperative electron beam therapy procedure with respect to cancer, the surgeon removes the bulk of a patient's tumor so that minimal residual disease remains. The attending radiation oncologist selects the electron beam energy and field size required to treat the target volume. A single radiation dose is then delivered to the tumor site, while the dose delivered to normal tissues is kept to a minimum. Examples of intraoperative electron beam therapy systems are disclosed in U.S. Pat. Nos. 5,321,271; 6,078,036, 5,661,377; 8,269,197; and 9,393,439; and in Assignee's co-pending PCT Patent Application No. PCT/US2017/020191.

During intraoperative treatment using electron beams, special tubes called applicators often are used to shape and guide the electron beam to the treatment site without allowing the beam to unduly expose healthy tissue. The treatment head which produces the electron beam must be accurately aligned to the applicator to deliver an accurate dose and to preserve beam symmetry and uniformity. Usually the applicator is fixed with respect to the treatment site, while the treatment head is actuated to achieve the desired docking configuration. The process of bringing the treatment head into alignment with the applicator is referred to as a "docking" procedure.

In one docking approach known as hard docking, the treatment head is brought into alignment with and directly attached to the applicator. Hard docking is not favored in many instances, in part due to safety concerns, because the applicator is simultaneously in contact with the patient and the relatively large and heavy treatment head of the treatment system. If the treatment head or patient is accidentally moved, the applicator may injure the patient. Also, a treatment head may use high voltage and/or current in some electron beam therapies, and avoiding direct contact between the treatment head and applicator is practiced to avoid a direct electrical connection between the treatment head and the patient.

In soft docking techniques, the treatment head is brought into a docking configuration in which the head is aligned with the applicator but does not physically contact the applicator. In most intraoperative electron beam therapies, soft docking is the preferred approach for achieving the desired docking configuration with maximum patient safety.

Many soft docking techniques have been practiced. One prior art soft docking approach uses laser fan beam alignment to a metal rod that is aligned to the axis of the applicator. The base of the rod and the top of the applicator are located on the machine's isocenter. The disk and rod docking scheme requires that the top of the applicator be at the machine's isocenter height and that the centerline of the applicator be in a plane perpendicular to the center of rotation of the treatment machine. Portable radiotherapy machines have no fixed isocenter position, and the patient plane is strictly determined by geometry, making the use of this scheme difficult.

In another prior art soft docking approach, multiple laser dots are aligned to a scribed line at the top of the applicator. The multiple laser dot docking scheme requires that eight dots from four pairs of lasers be made to coalesce into four dots on a circle scribed on the top surface of the applicator. Mutually orthogonal alignment motions produce similar behavior of the dots on the applicator surface. This makes it difficult to judge which motion of the treatment head will achieve alignment.

U.S. Pat. No. 6,078,036 describes a soft docking approach that uses lasers. While this approach is accurate, it is not automated. An operator uses lasers to generate docking feedback and then uses that feedback to manually guide the treatment head. The time to complete the docking process is variable and is dependent upon the skill, training, and experience of the operator.

Accordingly, there is a need for improved methods and apparatus for docking objects, particularly with respect to docking a medical treatment system to an applicator in the practice of electron beam therapies.

SUMMARY OF THE INVENTION

The present invention provides improved methods and apparatus that use machine vision techniques to rapidly and automatically guide objects into desired docking configurations. The present invention is based at least in part upon using multi-depth, rotationally symmetric targets that are observed from two or more observation perspectives. By taking advantage of parallax effects associated with the multi-depth topography of the target, the apparent positions of target features in captured image information encodes position and angular alignment of the objects relative to each other in three-dimensional space. The practice of the present invention provides a fast, accurate, reliable and automatic approach to achieve hard or soft docking configurations in the electron beam therapies. The present invention has been demonstrated to reduce the time required for docking by a significant factor over that achievable by a skilled manual operator.

The present invention is applicable to treatment sites everywhere in and on the body or body parts of living creatures, back, ear, shoulder, head, neck, whole body and internally. When implemented with respect to electron beam machines suitable for intraoperative electron beam therapy, the invention does not require a radiation-shielded vault but may be deployed in an ordinary room, such as a surgical suite, an outpatient clinic office, or other area that does not have additional radiation shielding. The invention may also be used outdoors in, on or under, land, sea or air, in a terrestrial or extra-terrestrial environment, and may operate for a time without benefit of externally provided power.

The invention applies generally to any accelerator system where the beam-axis, and the treatment axis are to be aligned either by moving the patient, or by moving the treatment head, or both. A specific application is for alignment of an electron beam system in IORT by mechanical actuation of the treatment head toward a patient lying on an operating room table. For example, when applied to IORT treatment, or any other treatment where the treatment field is defined by angle and position, as with an applicator, the present invention has utility in providing for automatic docking in angle and position.

Docking alignment may be achieved once in advance of treatment, or, may be an ongoing process ("tracking") taking place in real time during treatment, even in the presence of patient motion. The system used for alignment may also be used to provide beam inhibit signals, to enable "gating," in the presence of patient-motion detected via the imaging system.

Typical approaches to radiation therapy involve control of the dose distribution delivered, transversely and at depth, to ensure the required therapeutic dose is delivered to the tissue to be treated, while controlling and limiting the dose incidentally delivered to tissue not to be treated. Control of dose distribution for electron therapy in practice requires control of the electron phase-space distribution via control of accelerator parameters and post-accelerator beam processing typically via a collimator assembly incorporating one or several scattering foils as well as beam shaping surfaces, typically cylinders and/or cones. Alignment and positioning of the collimator according to this approach, therefore, affects symmetry and flatness of the dose profile at the treatment plane.

A typical tolerance on field flatness (homogeneity) is the following, applicable to the MOBETRON machine: The difference in intensities between minimum and maximum intensity points is ≤10% within the flattened region. The flattened region is defined as 1 cm inside the 90% isodose contour edges using the standard applicator. The standard applicator refers to a 10 cm circular zero degree tip angle applicator. In this context, beam and dosimetry specifications are defined in water, with this applicator and 50 cm source skin distance (SSD).

A typical tolerance on field symmetry is as follows, applicable to the MOBETRON machine: The difference in ratio of absorbed dose between any two points equidistant from the beam centerline within the flattened region is ≤2%. The symmetry is within the specified tolerance for all energies, gantry angles and for 0 degree circular applicator field sizes from 5 to 10 cm. Measurements should be averaged over an area of 1 cm$^2$.

These generally stringent requirements for flatness and symmetry impose tight tolerances on docking. Achievement of required beam quality in terms of symmetry and flatness is the major functional requirement of the docking system, after basic requirements such as safety. Typical tolerances of ±¼ degree and ±¼-mm, for example, are desirably met by a docking system. The present invention provides for fast and accurate alignment of the collimation axis to a treatment axis to meet such stringent docking tolerances if desired.

In one aspect, the present invention relates to an electron beam treatment system that automatically aims an electron beam with respect to a treatment site, said system comprising:
  a) an electron beam machine that emits an electron beam on an electron beam path;
  b) an applicator located with respect to the treatment site such that the electron beam is aimed at the treatment site through the applicator when the electron beam is properly aligned, said applicator having an applicator axis; and
  c) a machine vision system that automatically positions the electron beam machine at a position and angular alignment relative to the applicator to aim the electron beam through the applicator at the treatment site, said machine vision system comprising:
    i. a docking target coupled to the applicator and comprising a plurality of concentric facets having a common optical axis that is aligned with the applicator axis, wherein said common optical axis is aligned with the electron beam path when the electron beam is properly aimed at the treatment site, wherein the plurality of concentric facets comprise at least first and second facets, wherein at least one of the first and second facets of the docking target comprises imageable characteristics that encode a parallax disparity relative to reference image information that is indicative of an aim misalignment when the electron beam is improperly aimed at the treatment site, and wherein the imageable characteristics of at least one of the first and second facets encode a distance disparity relative to reference image information that is indicative of a distance error when the electron beam machine is at a distance from the docking target that is different from a desired distance,
    ii. first and second image capturing devices coupled to the electron beam machine in a manner effective such that each image capturing device observes and captures image information of the docking target from first and second observation perspectives, respectively, wherein at least first and second facets of the docking target are characterized by at least one of a different distance or a different angle of presentation with respect to the observation perspectives, and wherein the captured image information encodes information indicative of the alignment and distance of the electron beam machine relative to the applicator, and
    iii. a machine vision control system comprising program instructions that use the image information captured by the first and second image capturing devices to position the electron beam machine into a desired alignment and distance relative to the target in order to aim the electron beam at the treatment site.

In another aspect, the present invention relates to method of positioning and aligning a first object with a second object, comprising the steps of:
  a) locating a target with respect to the first object, wherein the docking target comprises a plurality of concentric facets having a common optical axis, wherein at least first and second facets comprise first and second imageable characteristics, respectively, wherein at least one of the first and second imageable characteristics encodes a parallax disparity when the docking target is viewed from a perspective that is different from a desired perspective, and wherein at least one of the first and second imageable characteristics encodes a distance disparity when the target is viewed from a perspective that is at a different distance from the docking target than a desired distance;
  b) locating first and second image capturing devices with respect to the second object;
  c) using the located first and second image capturing devices to observe and capture image information of the target from first and second perspectives, respectively; and
  d) using the captured image information to guide the first object into a desired position and angular alignment relative to the second object.

In another aspect, the present invention relates to a method of aiming an electron beam at a treatment site, comprising the steps of:
  a) providing an electron beam machine that emits an electron beam on an electron beam path;
  b) providing an applicator located with respect to the treatment site such that the electron beam is aimed at the treatment site through the applicator when the electron beam is properly aligned, said applicator having an applicator axis;

c) locating a docking target with respect to the applicator, wherein the docking target comprises a plurality of concentric facets having a common optical axis, wherein at least first and second facets comprise first and second imageable characteristics, respectively, wherein at least one of the first and second imageable characteristics imageable characteristics encode a parallax disparity relative to reference image information that is indicative of an aim misalignment when the electron beam is improperly aimed at the treatment site, and wherein the imageable characteristics of at least one of the first and second facets encode a distance disparity relative to reference image information that is indicative of a distance error when the electron beam machine is at a distance from the docking target that is different from a desired distance;

d) providing first and second image capturing devices coupled to the electron beam machine in a manner effective such that each image capturing device observes and captures image information of the docking target from first and second perspectives, respectively, wherein the captured image information encodes information indicative of the alignment and distance of the electron beam machine relative to the applicator, and e) using the image information captured by the first and second image capturing devices to position the electron beam machine into a desired alignment and distance relative to the target in order to aim the electron beam at the treatment site.

In another aspect, the present invention relates to a method of using an electron beam to treat a patient, comprising the steps of:

a) docking the electron beam system of claim 1 or 10 into a desired docking configuration with the patient; and b) while the electron beam system of claim 1 or 2 is in the desired docking configuration, using the electron beam system to irradiate a treatment site on the patient with an electron beam.

In another aspect, the present invention relates to a method of using an electron beam to treat a patent, comprising the steps of:

a) docking the electron beam system of claim 1 or 2 into a desired docking configuration with the patient;

b) while the electron beam system of claim 1 or 2 is in the desired docking configuration, using the electron beam system to irradiate a treatment site on the patient with an electron beam;

c) during step (b), monitoring information indicative of whether the electron beam system is in the desired docking configuration; and d) using the monitored information to disable the electron beam when the monitored information indicates that the electron beam system is not in the desired docking configuration.

In another aspect, the present invention relates to a method of using an electron beam to treat a patent, comprising the steps of:

a) docking the electron beam system of claim 1 or 2 into a desired docking configuration with the patient;

b) while the electron beam system of claim 1 or 2 is in the desired docking configuration, using the electron beam system to irradiate a treatment site on the patient with an electron beam;

c) during step (b), observing the docking target to capture image information of the docking target;

d) during step (b), using the image information in real time to provide signal information indicative of whether the electron beam system is in the desired docking configuration; and e) using the signal information to disable the electron beam when the signal information indicates that the electron beam system is not in the desired docking configuration.

BRIEF DESCRIPTION OF THE DRAWINGS

FIG. 3 shows a top view of the docking target used in the electron beam treatment system of FIG. 1.

FIG. 4 is a top perspective of the target of FIG. 2 in which the target is black anodized aluminum and ring-shaped patters are etched on three observable facets.

FIG. 4 shows a top perspective view of the docking target of FIG. 3.

FIG. 5 shows a perspective, side cross-section view of the docking target of FIGS. 3 and 4 taken through line A-A of FIG. 3.

FIG. 6 schematically shows a top view of a preferred deployment of machine vision cameras with respect to the docking target when the electron beam emitted by the electron beam treatment system of FIG. 1 is properly aimed at a treatment site.

FIG. 11c is a schematic view of the image of the docking target acquired by the second image capture device of FIG. 12a.

FIG. 12b is a schematic view of the image of the docking target acquired by the first image capture device of FIG. 13a.

FIG. 12c is a schematic view of the image of the docking target acquired by the second image capture device of FIG. 13a.

FIG. 13b is a schematic view of the image of the docking target acquired by the first image capture device of FIG. 14a.

FIG. 13c is a schematic view of the image of the docking target acquired by the second image capture device of FIG. 14a.

FIG. 14b is a schematic view of the image of the docking target acquired by the first image capture device of FIG. 15a.

FIG. 14c is a schematic view of the image of the docking target acquired by the second image capture device of FIG. 15a.

FIG. 15a is a side view along the y-axis schematically showing how first and second image capturing devices, and hence electron beam axis, of the system of FIG. 1 are shifted out of alignment with the docking target by rotation of the devices, and hence the electron beam axis, about the y-axis.

FIG. 15b is a top view along the z-axis schematically showing how first and second image capturing devices of the system of FIG. 16a are aligned with the docking target when the electron beam machine is at a proper distance from the docking target along the z-axis, but both the cameras are shifted out of alignment by rotation about the y-axis.

FIG. 15b is a schematic view of the image of the docking target acquired by the first image capture device of FIG. 15a.

FIG. 15c is a schematic view of the image of the docking target acquired by the second image capture device of FIG. 15a.

DETAILED DESCRIPTION OF PRESENTLY PREFERRED EMBODIMENTS

The present invention provides a machine vision system that automatically positions and aligns a first object to a second object. Optionally, an operator may oversee, adjust, enable, disable, or otherwise control or interact with the automated guidance. The use of machine vision to automatically position and align objects is useful in a wide range of applications, including to dock medical treatment machines in patient treatments, automated manufacture and assembly, vehicle (air, land, sea, or space) guidance, quality control, security, authentication, monitoring, and the like. For purposes of illustration, the principles of the present invention will be described with respect to using machine vision to automatically position and align electron beam treatment machines to carry out electron beam treatments.

Figure 1:
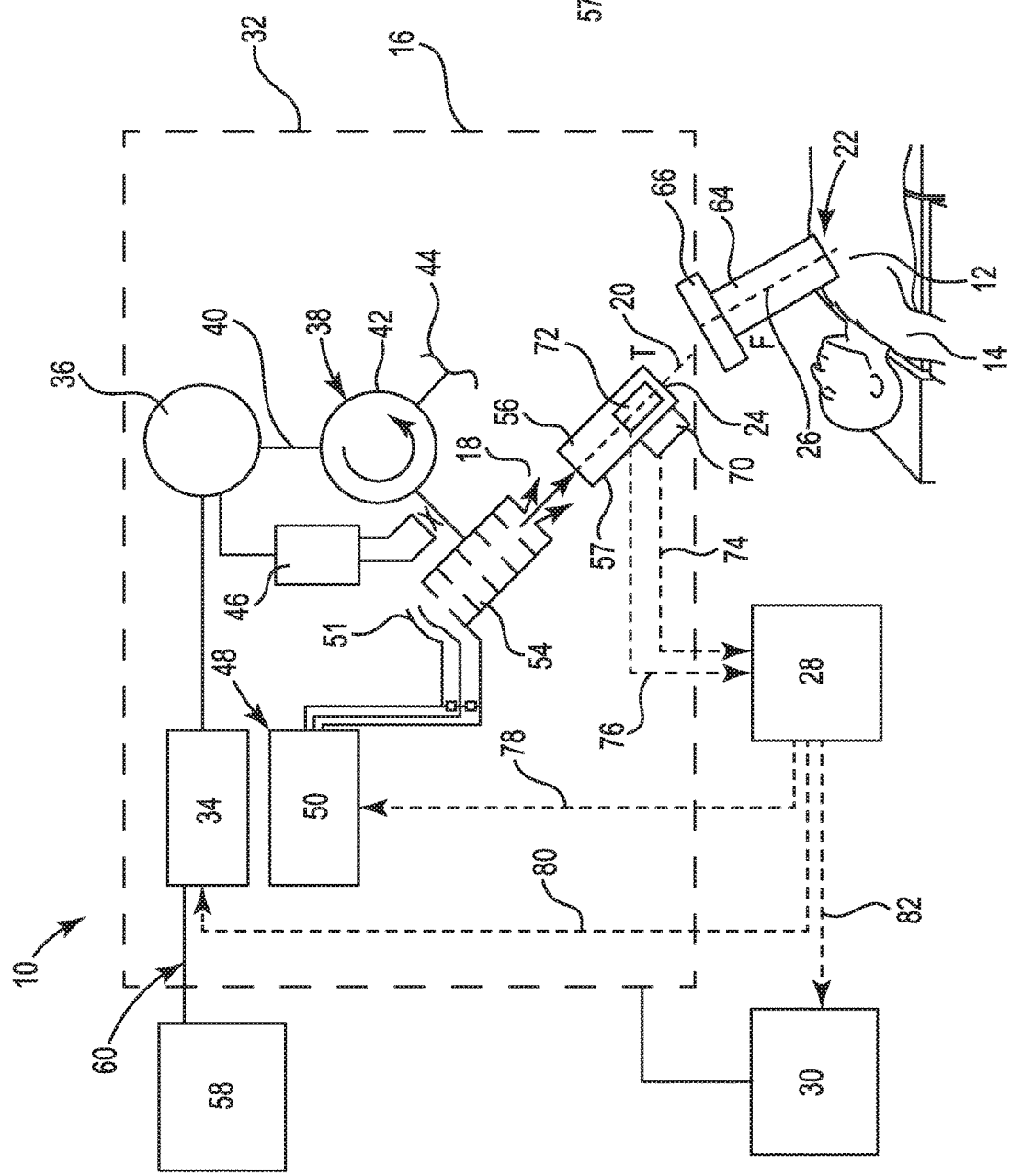
FIG. 1 shows an electron beam treatment system of the present invention that uses machine vision to automatically position and align an electron beam machine with an applicator through which the electron beam is aimed at a treatment site.

An exemplary embodiment of an electron beam (also referred to in the field of electron beam therapy as an "ebeam") radiation system 10 of the present invention is schematically shown in FIG. 1. Electron beam radiation system 10 is useful to irradiate a target site 12 on a patient 14 with a suitable electron beam radiation dose. As a consequence of irradiating target site 12 to the penetration depth, a target volume of patient 14 receives the desired irradiation dose. The use of electron beam therapies is further described in U.S. Pat. Nos. 8,269,197; 6,078,036; and Assignee's co-pending PCT Patent App. No. PCT/US2017/020191. Assignee's co-pending PCT Patent App. No. PCT/US2017/020191 describes technology that allows the dose and penetration depth of electron beam treatments to be controlled and adjusted in fine increments with great precision.

System 10 is useful for irradiating a wide range of treatment sites anywhere in or on body or body parts of the patient 14. For example, external treatments may involve treating the ears, nose, face, forehead, scalp, back, shoulders, neck, arms, hands, chest, abdomen, pelvic region, legs, or feet. Internal treatment sites may include the brain, blood vessels and/or arteries, heart, lungs, liver, colon, stomach, gall bladder, intestinal tract, glands, muscles, ligaments, tendons, bone, or the like. Internal sites may be exposed during a surgery to make the target site more accessible during a treatment. Due to the ability to control the shape and aim direction of the electron beam aimed at the target site 12, system 10 is useful for treating target sites with a variety of shapes and contours.

Many illustrative embodiments of system 10 are based on the use of technology platforms that use electron linear accelerators to deliver intraoperative electron beam radiation therapies (IOERT) in unshielded operating rooms. Such treatment platforms often are compact, lightweight, mobile, and self-shielded. For purposes of illustration, system 10 is shown as such a technology platform. Consequently, system 10 may be present and used intraoperatively at a location of a surgical or other care related procedure. This allows electron beam radiation to be applied before, during or promptly after surgery. Due to the time-sensitive nature of many therapeutic effects of electron beams, being able to apply irradiation intraoperatively in this manner is beneficial in many modes of practice.

System 10 is useful to carry out a wide range of treatments for which electron beam irradiation provides a treatment, benefit, or other desired effect for surgery or as an adjunct to surgery or other procedure. For example, system 10 may be used to treat cancer, dermatological conditions, and/or to provide cosmesis. Exemplary applications in the dermatological field include prevention or treatment of scarring of the dermis including hypertrophic scarring, dermal fibroproliferative lesions, and benign fibrous tumors such as keloids. In some embodiments, electron beam radiation may be used to treat or prevent scar formation resulting from breast cancer surgical procedures or reduce the severity of scar formation in emergency room procedures. Other exemplary applications include treatment for internal conditions such as surgical adhesions and restenosis, as may occur when a blood vessel is treated for blockage. For example, system 10 may be used to irradiate the microvasculature of the surgical bed to reduce the probability of formation of surgical adhesions. As another example, as an adjunct to vascular surgery, system 10 may be used to treat the anastomosis of blood vessels such as the femoral artery, popliteal artery and carotid artery to help prevent restenosis.

In some applications, electron beam radiation may be applied internally prior to closure of the wound, such as preventing surgical adhesions or in irradiating anastomosed blood vessels in vascular surgery to prevent restenosis. In some applications, such as scar amelioration, it is beneficial to irradiate the closed incision promptly. For example, system 10 can be used to deliver electron beam radiation dose(s) in a time period ranging from 0 to 24 hours, or even 0 to 5 hours, or even 0 to 1 hour, or even 0 to 30 minutes of the time of a surgery. This ability to apply irradiation treatments promptly is contrasted to treatments that use very large and immobile machines housed in separate, heavily-shielded environments that are remote from the treatment location. Radiation treatment in such large, remotely housed machines has been applied post-operatively after a delay of hours or days, thereby missing the opportunity to achieve the optimal benefits of electron beam radiation therapy.

Electron beam radiation system 10 of FIG. 1 generally includes an electron beam generation machine 16 that emits a linearly accelerated, straight through electron beam 18. In illustrative embodiments, the electron beam systems provide irradiation doses of up to about 20 Gy, such as up to about 15 Gy, up to about 10 Gy, up to about 5 Gy, or up to about 2 Gy. In certain embodiments, the electron beam systems provide radiation to the target site 12 at a rate of at least about 0.2 Gy/min, at least about 1 Gy/min at least about 2 Gy/min, at least about 5 Gy/min, or at least about 10 Gy/min.

Electron beam machine 16 may be operated to deliver electron beams with energy selected within a wide range, such as 0.5 MeV to 22 MeV in illustrative embodiments. The operating ranges of about 6 MeV or less generally are associated with lower levels electron beam energy in the field of electron beam therapy. Undue bremsstrahlung production can be avoided with careful attention to avoid unnecessary objects in the path of the electron beam. Certain objects, however, are beneficially presented to the electron beam, such as scattering foils, windows, absorbers (described further below), sensors, ion chambers and the like.

Still referring to FIG. 1, electron beam generation machine 16 generates electron beam 18, processes and shapes the beam 18, and then emits the beam 18 along an electron beam path having central electron beam axis 20. The goal of using machine vision is to automatically position and align machine 16 so that the electron beam 18 is aimed at the treatment site 12 through applicator assembly 22. When the desired alignment and position with the applicator assembly 22 is achieved, machine 16 is said to be "docked" with the applicator assembly 22. Docking may be hard or soft Hard docking refers to a state in which there is direct physical contact between the electron beam machine 16 and applicator assembly 22. Although hard docking may be used, its use is disfavored in many treatments because the applicator assembly 22 is then physically coupled to both the patient 14 and the machine 16. If the machine 16 were to be moved, this could injure the patient or disrupt the treatment set-up. Also, direct contact creates a risk of electrically coupling the machine 16 to the patient, which may be undesirable when machine 16 is operating in some voltage and current ranges.

Soft docking often is more favored and occurs when the machine 16 is properly aligned and positioned but without direct contact with applicator assembly 22 or any other item in contact with the patient. Even though soft docking involves a distance or gap between the outlet 24 of machine 16 and applicator assembly 22, the electron beam dose is still effectively and more safely delivered to the treatment site 12. For purposes of illustration, system 10 uses soft docking techniques.

Docking is achieved when (1) the distance, d, between the outlet 24 matches a desired distance and (2) the electron beam axis 20 is aligned in a desired manner (e.g., co-linear and not merely parallel) with the applicator assembly axis 26. For purposes of illustration, machine 16 is not yet properly docked with the applicator assembly 22 in FIG. 1. The distance, d, between outlet 24 and applicator assembly 22 is too great. The machine also is displaced (too far to the left in FIG. 1). Further, the electron beam axis 20 is not yet aligned with the applicator assembly axis 26 but rather is misaligned by an angle θ (theta). Advantageously, machine vision principles of the present invention are used to automatically and rapidly bring the electron beam machine into the desired, properly docked position.

As seen in FIG. 1, electron beam machine is coupled to a controller 28 that implements machine vision control. Responsive to control signals from controller 28, one or more actuation devices 30 guide electron beam machine 16 into proper docking configuration with applicator assembly 22. Desirably, controller 28 and actuation devices 30 are able to guide machine 16 on at least two translational axes and at least two rotational axes. More preferably, controller 28 and actuation devices 30 are able to guide machine 16 on three translational axes and at least three rotational axes to provide control and actuation of six degrees of freedom.

For purposes of implementing automatic docking using machine vision principles, x, y, z, pitch, roll, and yaw axes are identified. First, one side of electron beam machine 16 may be designated as the front side for reference purposes. Facing the designated front side, the x-axis refers to the side-to-side axis from this observation perspective. X-axis control refers to translation to the right or left along the x-axis. The y-axis refers to the front-to-back axis from this perspective. Y-axis control refers to translation forward or backward along the y-axis. The Z-axis is the vertical up and down axis from this perspective. Z-axis control refers to translation up or down on the z-axis. Machine 16 also may rotate via pitch, roll, or yaw. Pitch refers to rotation about the x-axis so that the machine 16 pitches forward or backward. Pitch control involves controlling rotation about the pitch axis. Roll refers to rotation about the y-axis so that the machine dips right or left. Roll control refers to controlling rotation about the y-axis. Yaw refers to rotation about the z-axis so that the machine 16 rotates sideways right or left Yaw control refers to controlling rotation about the z-axis. Preferred modes of control of the present invention involve the ability to control movement of machine 16 in all six of these degrees of freedom (i.e., control of translation with respect to the x-axis, y-axis, z-axis, and control of pitch, roll, and yaw with respect to the x-axis, y-axis, and z-axis).

Still referring to FIG. 1, electron beam generation machine 16 generally includes housing 32 that contains a modulator 34, microwave source 36, a microwave network 38, an electron source 48, a linear accelerator 54, and a collimator assembly 56. An external power supply 58 supplies power to the modulator 34 via power cable 60. FIG. 1 shows controller 28, actuation devices 30, power supply 58, and power cable 60 as separate components from machine 16, but one or more of may be integrated into machine 16 if desired. For example, power supply 58 and power cable 60 as an option may be included inside housing 32 along with other components.

The present invention is useful with different types of electron beam machines, including those that generate so-called linear (or straight through) electron beams as well as bending systems. The docking strategies of the present invention are useful regardless of the actuation format. For purposes of illustration, electron beam generation machine 16 as shown in FIG. 1 is the type that uses linear acceleration techniques to boost electron beam energy to desired levels. Consequently, electron beam 18 is aimed along substantially linear electron beam axis 20 from accelerator 54 straight through applicator assembly 22 to the target site 12. Electron beam generation machine 16 may be referred to in the industry as a "straight through" type of system. The use of linear accelerator structures to generate electron beams for therapeutic uses is well known. As known in the art, a straight through system aims an electron beam at a target site along a generally linear path from the exit window (not shown) of the linear accelerator 54 straight through to the target site 12. This helps to ensure use of much of the beam current produced.

Examples of such linear electron beam therapy treatment systems suitable for intraoperative procedures are described in U.S. Pat. Nos. 5,321,271; 6,078,036, 5,661,377; 8,269,197; and 9,393,439; and in Assignee's co-pending PCT Patent Application No. PCT/US2017/020191, all of which are assigned to IntraOp Medical Corporation. Another example of such a system suitable for intraoperative procedures is the electron beam machine commercially available from IntraOp Medical Corporation under the trade designation MOBETRON. Generally, linear, straight-through systems such as these are a result of engineering a compact linear accelerator that can fit when vertical under ceiling heights common to many procedure sites such as treatment rooms or surgery rooms.

Modulator 34 receives power from the power output of power supply 58 via cable 60. Power supply 58 may be any suitable source of electricity. Power supply 58, as an option, may be a component of a continuous source of electricity from a power utility. Alternatively, power supply 58 may be battery powered, permitting untethered operation of electron beam generation machine 16. Modulator 34 accepts the power from power supply 58 (which may be line power, battery power or any suitable power source), and converts it to short pulses of high voltage that it applies to the microwave source 36. Microwave source 36 converts the voltage into microwave or radio frequency (RF) energy.

Examples of suitable microwave sources for use as microwave source 36 include a magnetron or a klystron to power linear accelerator 54. When a klystron is used, an input signal is provided from an "RF driver," e.g., a pulsed 200-Watt (W) RF power source. A magnetron is preferred based on cost and ease to incorporate into the system 10.

Many suitable embodiments of a magnetron operate using X-band, S-band, or C-band frequencies. X-band devices are more preferred, as other embodiments of machine 16 tend to be heavier when using S or C band devices. X-band frequency technology also tends to minimize the diameter, and hence the weight, of the accelerator structure. One illustrative example of a suitable magnetron operating at X-band frequencies is the Model L-6170-03 sold by L3 Electron Devices. This magnetron is capable of operating at a peak power of about 2.0 megawatt (MW) and 200 W of average power.

Microwave network 38 conveys the microwave or RF power from the microwave source 36 to the linear accelerator 54. The microwave network 38 often typically includes a waveguide 40, circulator 42, a load 44, and an automatic frequency control (AFC) system 46. The use of these components in an accelerator system is well known to those skilled in the art and has been described in the patent literature. See, e.g., U.S. Pat. No. 3,820,035. Briefly, microwaves from the RF source passes through the circulator 42 before entering the accelerator 54 to protect the RF source from reflected power from the accelerator 54. Instead, the power not absorbed in the accelerator 54 is reflected back into the circulator 42 and shunted into a water-cooled or air-cooled dummy load 44. An AFC system 46 is used to keep the magnetron tuned to the accelerator resonance microwave frequency.

Microwave or RF power may be injected into the accelerator structure through a fixed waveguide 40 if the microwave source 36 (e.g., a magnetron) is mounted on a rigid assembly (not shown) with the linear accelerator 54. Alternatively, a flexible waveguide 40 may be used in the microwave network 38. As one option, microwave or RF power supplied to the linear accelerator 54 through microwave network 38 may be modulated in the case of a magnetron by varying the pulsed high voltage supplied to the magnetron from power supply 58. Modulating the voltage of the power supply 58 in this manner allows the energy level, and hence penetration depth, of the electron beam 18 to be controlled and adjusted to many different desired settings with excellent precision using appropriate feedback strategies such as those described in Assignee's co-pending PCT application No. PCT/US2017/020191. For a klystron, the same approach may be used. Alternatively, the input microwave power to the klystron may be varied.

In parallel with microwave source 36 supplying microwave or RF energy to linear accelerator 54, electron source 48 supplies electrons to linear accelerator 54. Electron source 48 typically includes an electron gun driver 50, an electron gun 52, and features that couple the gun 52 to the linear accelerator 54. Many different embodiments of electron guns are known and would be suitable. For example, some embodiments use a diode-type or triode-type electron gun, with a high-voltage applied between cathode and anode. Many commercially available electron guns operate at voltage ranges between 10 kV to 17 kV, though electron guns 52 operating at other voltages may, in some embodiments, also be used. The voltage often is either DC or pulsed. In the case of the triode-type gun, a lower grid voltage also is applied between the cathode and grid. The grid voltage can disable or enable the beam, and the grid voltage may be varied continuously to inject more or less gun current. The grid voltage may optionally be controlled through a feedback system. A skilled worker in the field of linear accelerator engineering is able to understand and choose an appropriate gun design suitable for the linear accelerator 54 to be used.

One example of a commercially available electron gun suitable in the practice of the present invention has been sold by L3 Electron Devices (formerly Litton) under the product designation M592 Electron Gun. The injector cathode of this particular gun operates in some embodiments at 10 to 14 kV and has a very small diameter emitting surface. This design is intended to provide low emittance and good capture efficiency while maintaining low energy spread. Typical pulse widths for operation may be in the range from 0.5 to 6 microseconds.

The RF source is pulsed by a modulator 34. It is preferred that the modulator 34 be solid state based rather than tube based to reduce weight and improve portability. The pulse repetition frequency (PRF) may vary from about 10 to about 240 pulses per second and the pulse width from about 1 to 4 microseconds. The combination of PRF and pulse width is one factor that impacts the dose rate of the emerging electron beam. For diode-gun systems, the gun likewise may be pulsed by the same modulator system, albeit with an intervening gun transformer to permit a step in voltage.

Linear accelerator 54 is configured to receive the microwave or RF power from the microwave network 38. Linear accelerator 54 also is configured to receive the electrons from the electron source 48. Linear accelerator 54 is coupled to the microwave network 38 and the electron source 48 in a manner effective to use the microwave or RF power to accelerate the electrons to provide electron beam 18 having an energy in the desired operating range, e.g., from 0.1 MeV to 22 MeV, preferably 0.5 MeV to 15 MeV, more preferably 4.0 MeV to 15 MeV, and even more preferably 6, 9, and 12 MeV. As used herein, the energy level of the electron beam refers to the energy of the electron beam at the patient plane (as would be determined by a specified QA protocol according to conventional practices), unless otherwise expressly stated. For example, in one mode of practice using a MOBETRON machine, the electron beam energy before the collimator section is 12.5 MeV, which provides 12 MeV energy at the treatment site 12.

A variety of different linear accelerator structures would be suitable in the practice of the present invention. For example, linear accelerator 54 may have a structure that implements any of a variety of different cavity coupling strategies. Examples of suitable structures include those that provide side cavity coupling, slot coupling, and center hole coupling. CJ. Karzmark, Craig S. Nunan and Eiji Tanabe, Medical Electron Accelerators (McGraw-Hill, New York, 1993). Linear accelerator 54 also may have a structure that implements a variety of different symmetry strategies. Examples of suitable structures include those that provide periodic, bi-periodic, or tri-periodic symmetry. Examples of suitable accelerator structures also may implement a range of standing wave or travelling wave strategies. Examples of suitable linear accelerators 54 also may be selected to operate with many different bands of microwave or RF power. Examples of suitable power bands include S-Band (2-4 GHz), C-Band (4-8 GHz), X-Band (8-12 GHz), and still higher frequencies. David H. Whittum, "Microwave Electron Linacs for Oncology", Reviews of Accelerator Science and Technology, VoL 2 (2009) 63-92. In some illustrative embodiments, the linear accelerator 54 uses a low profile structure design, incorporating on-axis bi-periodic cavities operated at X-band frequencies. U.S. Pat. No. 8,111,025 provides more details on charged particle accelerators, radiation sources, systems, and methods, side-coupled X-band accelerators and on-axis and side-coupled S-band and C-band accelerators are other suitable examples.

The linear accelerator 54, its attached electron source 48, and one or more other components of electron beam generation machine 16 may be mounted inside housing 32 on a strongback (not shown) or other suitable support member. The linear accelerator 54 and electron source 48 may be encased in lead or other shielding material (not shown) as desired to minimize radiation leakage. The higher the resonant frequency of the accelerator guide, the smaller is the diameter of the structure. This results in a lighter-weight encasement to limit leakage radiation. An advantage of linear, straight through machines is that the shielding requirements are less severe than machines that using beam bending strategies. This allows straight-through electron beam radiation machines to be deployed for intraoperative procedures rather than being deployed in remote locations inside heavily shielded rooms.

During operation, at least the network 38, the linear accelerator 54, and the microwave source 36 may experience heating. It is desirable to cool machine 16 (particularly the units 36, 42, 44, and 46) in order to dissipate this heat. A variety of strategies can be used to accomplish cooling. For example, accelerator structure 76 and microwave source 36 can be water-cooled as is well known. In some preferred embodiments, air-cooling is preferred as air cooling reduces weight and minimizes servicing issues. The practice of the present invention permits operation at low-duty cycle, for which air-cooling would be quite adequate. Air cooling works in such embodiments because magnetron average power, e.g., 200 W in an illustrative embodiment, is relatively low for electron beams. In contrast, X-ray machines typically involve average power in the range from 1 kW to 3 kW. The ability to use air cooling with electron beams is one factor that helps preferred electron beam machines of the present invention to be so compact and lightweight. The result is that the corresponding system 10 (see FIG. 1) is easier to deploy and use in intraoperative procedures.

An exit window (not shown) desirably is provided at the interface between linear accelerator 54 and collimator assembly 56. An exit window at the beam outlet of linear accelerator 54 is used to maintain a vacuum within the accelerator 54. The window should be strong enough to withstand the pressure difference between the accelerator vacuum and the ambient atmospheric pressure, e.g., a difference of about 15 pounds per square inch (psi) in some instances, but should be thin enough to avoid excessive beam interception, scattering and/or energy loss (principally through bremsstrahlung production). Balancing these factors, the window may be formed of titanium in many embodiments. Alternatively, beryllium or other metallic or composite materials also may be used.

In some modes of practice, system 10 may incorporate feedback control strategies as described in Assignee's co-pending PCT Application No. PCT/US2017/020191 in order to adjust electron beam energy in fine increments with high precision, even at lower electron beam energy levels. To implement such feedback strategies, one or more sensors (not shown) may be deployed in or around collimator assembly 56 in order to detect two or more independent characteristics of the beam. Other sensor deployments, including deployments in the beam path or other locations downstream from exit window may be used, if desired.

The accelerated electron beam exits the linear accelerator 54 through the exit window (not shown) and next continues on a linear path through collimator assembly 56 that receives, broadens, and flattens the beam. Collimator assembly 56 can include a housing 57. Housing 57 may be constructed of materials that help contain leakage radiation, principally bremsstrahlung radiation, or the collimator design itself could be sufficient to contain the leakage radiation. A scattering foil system (not shown) and at least one transmission radiation detector (not shown) often are housed in collimator assembly 56. Regulatory requirements for medical products such as this typically require one transmission type detector after foils and scattering elements, and one additional, redundant radiation detector.

Most typically both detectors are of the ionization chamber type, used in transmission, and located after the last scattering foil. A scattering foil system serves multiple functions. For example, electron beam systems typically produce beams of small transverse dimension, on the order of 1 mm to 3 mm across, much smaller than typical treatment fields. A scattering foil system helps to broaden the electron beam 18. The scattering foil system 82 also helps to flatten electron beam 18 at the treatment plane of treatment site 12. In many modes of practice, the beam 18 passes through the scattering foil system to help in shaping of the isodose curves at the treatment plane at target site 12.

In illustrative modes of practice, a scattering foil system also helps to enlarge the accelerated beam 18 from being several square millimeters in cross section to several square centimeters in cross section. Uniformity of dose across the treatment field is a desired goal to simplify dose planning for therapeutic applications. For example, collimator assembly 56 with or without applicator assembly 22 may function to provide a flat electron beam dose profile such that the coefficient of variation of the beam dose across the full width at half-maximum (FWHM) of the beam is less than ±50%, less than ±40%, less that ±30%, less than ±20%, less than ±10%, less than +5%, less than ±2.5%, or less than ±1%. In some embodiments, the collimator may function to broaden the electron beam to field sizes that are 1 cm to 25 cm across.

A typical scattering foil system includes at least one, even two or more, and even three or more scattering foils (not shown). The distance between the two or more foils is a design variable, depending on the energy range of the unit, the field size needed for the treatment application, and the geometry and materials of the mass elements in the treatment head. Generally, electron scattering foils may be designed using techniques such as empirical design iteration or Monte Carlo simulations. Other means of providing uniformity could rely on magnetic phenomena. For example, steering coils could be employed to raster the beam across a programmed area. Alternatively, a quadrupole magnet system could be used to modify the beam size at the target plane.

An ion chamber 84 serves multiple functions. In one aspect, an ion chamber 84 monitors the radiation dose delivered by the system and radiation when the prescribed pre-set dose is delivered. The monitor features of an ion chamber 84 may be segmented transversely to provide a reading of beam position in the transverse plane. This reading may be used in a feedback control system to provide current to steering coils upstream, so as to steer the beam and continuously correct any beam offset or symmetry error. Advantageously, this reading may be used in an innovative feedback control system (described in Assignee's co-pending PCT Application No. PCT/US2017/020191) used to control the electron beam energy, and hence penetration depth at the target site, with excellent precision. As another function, an ion chamber 84 may be used to terminate the beam and limit the amount of radiation received at the target site if an issue with the electron beam is detected. For example, a loss of a scattering foil could result in delivery of an excessive dose. In this fashion, an ion chamber 84 and associated electronics provide protective interlocks to shut down the beam under such circumstances.

To help provide machine vision functionality, first and second image capture devices 70 and 72 are mounted to the machine 16 in a manner effective to observe and capture image information of docking target 66 incorporated into applicator assembly 22. Each of the first and second image capture devices 70 and 72 may be configured to capture still images, video images, spectroscopic images, infrared images, and/or other image information of docking target 66.

Devices 70 and 72 observe docking target 66 from first and second observation perspectives, respectively. Image information captured by each device 70 and 72 encodes information indicative of the position (e.g., distance) and angular alignment of electron beam machine 16 with respect to the docking target 66 on applicator assembly 22. Individually, each observation provides the most sensitivity to position and angular alignment differences with respect to a single axis in the image plane. Collectively, the two observations provide excellent sensitivity to position and angular alignment differences on two different axes to allow for excellent precision in guiding the position and angular alignment of machine 16 relative to applicator 22 in three dimensional space. More image capture devices and more perspectives could be used if desired, but using two devices and two different observation perspectives in this manner provides sufficient information to accurately and rapidly guide machine 16 into a proper docking position without more perspectives being needed. Observation redundancy may be desirable in some instances, however, in which case more image capture devices and observation perspectives could be used.

Figure 7:
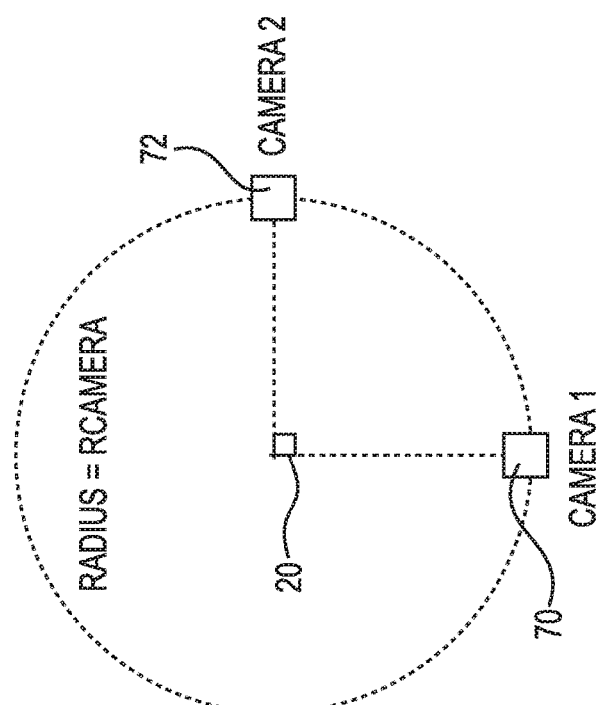
FIG. 7 schematically shows a preferred deployment of machine vision cameras in the electron beam treatment system of FIG. 1.

Image capture devices 70 and 72 may be deployed in any two positions such that each observes target 66 from a different perspective. However, an orthogonal, co-planar deployment of devices 70 and 72 as shown in FIG. 7 is preferred, as this provides position and angular alignment sensitivity on two different, orthogonal image plane axes. Orthogonal sensitivity with a 90 degree angular separation between devices 70 and 72 is believed to be optimum for machine vision guidance in three-dimensional space. Other deployments also may be used, such as camera separation in the range from about 10 degrees to 180 degrees. As shown in FIG. 7, image capture devices 70 and 72 are rigidly attached to machine 16 and arranged such that each device 70 and 72 observes from a perspective whose optical axis is centered on a reference circle 84 having a radius designated as $R_{camera}$. The center of reference circle 84 intersects the electron beam axis 20. This means that the observation origin of each device desirably is equidistant from the centrally located electron beam axis 20. The observation perspective of devices 70 and 72 also desirably are coplanar so that the plane of reference circle 84 desirably is orthogonal with the electron beam axis 20 as well.

Further, the deployment of devices 70 and 72 also is coordinated with target features of target 66 when machine 16 is properly docked, as is described further below. Implementing device deployment with such correlations with the electron beam axis 20 and target 66 makes it easier to implement machine vision guidance. Calibration and operation of devices 70 and 72 could be accomplished if device deployment is not coordinated in this way with the electron beam axis 20 and the target 66, but the calibration and operation would be more complex.

Referring again to FIG. 1, image capture devices 70 and 72 are coupled to controller 28 by data connection pathways 74 and 76. An illustrative implementation of machine vision functionality using devices 70 and 72 and such connectivity is described further below. In addition to machine functionality, other control functions of system 10 may be guided by controller 28. For example, controller 28 may be coupled to electron gun driver 50 by control connection 78 to guide electron source operation. Additionally, controller 28 may be coupled to modulator 34 by control connection 80 to guide operation of modulator 34. Further, controller 28 may be coupled to actuation device(s) by control connection 82 to control these devices as machine 16 is moved into a proper docking configuration relative to applicator assembly 22. Pathways 74, 76, 78, 80, and/or 82 may be independently wireless or wired. Wired connections are preferred for robust connectivity.

The accelerated and collimated electron beam is aimed at target site 12 through applicator assembly 22. The applicator assembly 22 is configured so that the electron beam 18 continues on a linear electron beam path straight through to the target site 12. In many modes of practice, the applicator assembly 22 further helps to define the shape and flatness of the electron beam 18. Applicator assembly 22 also makes it easier to aim the electron beam 18 while minimizing the manipulation of; contact with, or disturbance of the patient or target site 12. Furthermore, the use of applicator assembly 22 helps to avoid stray radiation and minimizes the dose delivered to healthy tissue by confining the radiation field.

Applicator assembly 22 is positioned proximal to the exit end 62 of collimator assembly 56. The gap between applicator assembly 22 and collimator assembly 56 is helpful for patient safety, for electrical isolation and for collision avoidance in the presence of both machine and patient motion. However, a smaller gap, or a shielded gap between assemblies 22 and 56 is beneficial to reduce radiation leakage in the operating room. The present invention aids the goal of minimal gap and/or a non-contact leakage shielding housing by facilitating tracking and auto-docking with respect to the applicator face (target 66 described further below). This helps to allow practice of real time active collision avoidance during auto-docking and also during a procedure after an initial docking is achieved, where an impending collision due to patient motion could be avoided by gantry motion away, combined with beam inhibit (gating) functionality. Thus the present invention overcomes the disadvantages of one conventional approach that attempts to minimize or avoid a gap between the collimator assembly 56 and applicator assembly 22 to eliminate or reduce stray electrons that could be scattered through the gap that could result in undue stray radiation in the ambient room.

In many modes of practice, the distance from the exit end of the applicator assembly 22 (or the end of optional field defining shield, if present) to the surface of the target site 12 can vary from contact with the target site 12 to distances up to about 10 cm from the patient surface. The distance can be determined by any suitable measurement technique such as by either mechanical measurement or an electronic rangefinder. In some modes of practice, applicator assembly 22 may be held in a desired position by a separate structure (not shown) that holds applicator assembly 22 in a fixed alignment with the treatment site 12 and patient 14. The applicator assembly 22 desirably is electrically isolated from other components of system 10, particularly in treatments in which the applicator contacts or is close to the patient 14.

Applicator assembly 22 generally includes applicator 64, docking target 66 used to help implement machine vision functionality in accordance with principles of the present invention, and an optional field-defining shield (not shown). Applicator assembly 22 may include other optional components to help further modify the electron beam 18 depth-dose (energy) or flatness. For example, energy reduction with low bremsstrahlung can be achieved by interspersing thin (0.5-1 mm) sheets of plastic or sheets made from low atomic number material into the applicator assembly 22 in a slot provided to accept them. (U.S. Pat. No. 8,269,197, "Method and system for electron beam applications") Materials with higher electron density also may be used and could be thinner for the same absorption. The applicator assembly 22 could also incorporate element(s) to act as a secondary scattering component. These may be made from suitable shaped low atomic number materials that help to further scatter electrons within the volume of applicator assembly 22. Examples of such materials, but by no means exclusive to these materials, include aluminum, carbon, and copper and combinations of these. These can be located in applicator assembly 22 at positions determined by Monte Carlo calculations or empirically for the energies and field size needed for the application.

In some modes of practice, a transparent or partially transparent applicator 64 may be beneficial. For example, such an applicator design may allow easier viewing of the treatment site. Applicators fabricated at least in part from PMMA, quartz, or the like would permit such viewing.

The applicator 64 may have a variety of shapes, such as being shaped to produce circular, square, irregular, or rectangular fields on the target site. One example of an applicator design, called a scan horn, creates long narrow fields by having scattering elements within the applicator that scatter electrons preferentially along the length of the field. In some embodiments, the scan horn may be used to confine the irradiated area to a strip of from about 2 cm to about 10 cm in length, and about 0.2 cm to about 1 cm in width.

Target 66 is attached to applicator 64 and includes a multi-faceted surface whose changing distances and/or angles of presentation to the first and second image capturing devices 70 and 72 allow imageable characteristics formed on the facets that individually and collectively encode position and angular alignment information upon observation. Advantageously, the changing distances and/or angles of presentation allow parallax effects to increase sensitivity of observations to both translational and rotational disparity from the desired docking configuration(s). For example, annular patterns with clearly defined edges are suitable imageable patterns that encode such information.

Figure 2:
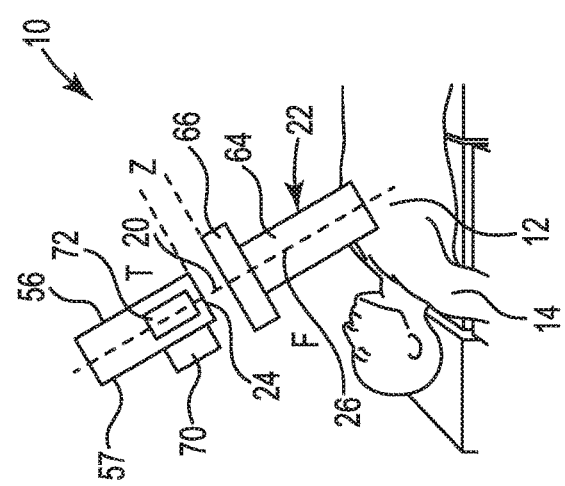
FIG. 2 shows a portion of the electron beam system of FIG. 1 where the electron beam machine is soft-docked to align the electron beam machine with the applicator.

FIG. 1 shows system 10 in a configuration in which machine 16 is not yet in a desired docking position with respect to applicator assembly 22. Machine vision principles of the present invention can be used to automatically and rapidly bring machine 16 into a desired docking configuration relative to applicator assembly 22 as shown in FIG. 2. In FIG. 2, exit end 62 is at a desired distance, d, corresponding to the desired docking configuration. Further, the electron beam axis is aligned and co-linear with the applicator assembly axis 26.

In actual practice, automated guidance using machine vision principles may be implemented by any suitable relative movement between the first object, in this case the applicator assembly 22, and the second object, in this case all or part of machine 16. In electron beam therapy, it is more typical that the applicator assembly 22 is fixed and all or a portion of machine 16 is moved to accomplish the desired docking configuration of FIG. 2.

FIGS. 3, 4, and 5 show details of a preferred embodiment of target 66 in more detail. Target 66 has an annular body 90 and is shown with preferred features that are characterized by corresponding concentric, annular features formed on body 90 so that target 66 is rotationally symmetric. This provides target with rotational invariance so that this preferred embodiment of target 66 presents the encoded information about positional disparity and rotational disparity from any approach angle. Advantageously, the top face 92 of target 66 presented to optical imaging devices 70 and 72 is multi-faceted so that two or more facets present radially symmetric, imageable patterns that have unique distances and angles of presentation, respectively, to the optical imaging devices 70 and 72 that observe the facets.

In addition to top face 92, annular body 90 includes bottom face 94, outer wall 96, and inner wall 98 defining central aperture 100. Electron beam 18 is aimed through aperture 100 at treatment site 12 when electron beam axis 20 and applicator axis 26 are aligned and co-linear. The lower outer rim 104 of bottom face 94 is configured with a rabbet 106 for weight savings. This rabbet 106 also provides a way to connect target 66 to applicator 64.

Top face 92 is formed with annular groove 108 that defines outer facet 110, middle, lower facet 112, and inner facet 114. Patterns with imageable characteristics are formed on facets 110, 112, and 114. Sidewalls 116 and 118 also are facets resulting from annular grove 108 but do not bear imageable patterns in this embodiment. In alternative modes of practice, such as when sidewalls 116 and 118 are angled facets rather than vertical relative to facets 110, 112, and 114, patterns with imageable characteristics may be deployed on the sidewalls. The edges between facets are desirably distinct to avoid any unduly rounded boundaries that could cause undue specular reflections that would unduly interfere with observing the edges of the imageable characteristics.

In this embodiment, facets 110 and 114 are co-planar, while facet 112 is on a different plane at the bottom of annular groove 108. Thus, facets 110 and 114 are on a first plane, whereas facet 112 is on a second plane. The first and second planes are parallel, but one of these could be angled relative to the other, if desired. Although the facets 110, 112, and 114 could be deployed on three different planes and/or three different angles with respect to observation by optical imaging devices 70 and 72, deploying patterns with imageable characteristics on the two different, parallel planes provides sufficient information to exploit distance and parallax effects to guide electron beam machine 16 to a desired docking configuration.

Concentric, annular patterns 120, 122, and 124 with imageable characteristics are formed on facets 110, 112, and 114. The annular shape of these patterns allows the patterns to be rotationally symmetric from any approach direction. Patterns 120, 122, and 124 are formed so that their respective inner and outer edge boundaries are sharp and well-defined for easy edge detection. The result is that apparent intra-pattern dimensions between edges of a single pattern as well as inter-pattern dimensions call translational and rotational disparities to be determined upon observation. These disparities can be used to generate control signals that are used to guide machine 16 into a desired docked position.

Patterns 120, 122, and 124 desirably are formed so that high contrast exists between the patterns and regions of target 66 outside the patterns. Contrast can be determined via different visual imaging methods. For example, a black/white camera could use a single channel to measure the intensity of light from an object. Boundaries of imageable characteristics are found from the contrast between low intensity (dark) and high intensity (light) regions. Color imaging also may be used. A typical color camera has 3 channels, red, blue, and green. A system using color cameras could evaluate by looking at changes from one channel to another such as from red to green, etc. Yet another way to use color contrast would be to convert RGB values to HSV (hue, saturation, value) representation and then look for contrast in the hue channel. Use of color or IR imaging techniques also may help to discriminate against imaging artifacts such as may arise due to background lighting High contrast allows the locations of the edges to be determined with high accuracy using machine vision. Desirably, both the pattern regions and areas outside the patterns are provided in a way that minimizes specular reflections, as such reflections can make accurate edge detection more difficult. Ideally, the facets of target 66 would have a Lambertian surface finish to minimize such specular effects. In theory, a Lambertian surface for reflection is a surface that appears uniformly bright from all directions of view and reflects all of the incident light Lambertian reflectance is the property exhibited by an ideal matte or diffusely reflecting surface. In actual practice, the facets are made to be as matte, or as diffusely reflecting, as is practical. Surfaces with a matte finish are suitable so long as the edge boundaries of the patterns 120, 122, and 124 can be identified to a desired degree of accuracy by optical imaging.

FIG. 3 shows that the central pattern 122 has an average radius, $R_{target}$. The central pattern 122 having the average radius $R_{target}$ may be used in preferred embodiments as a nominal target to align optical imaging devices 70 and 72 to achieve a desired docking configuration. Calibration and use of target 66 is simpler when $R_{target}$ and $R_{camera}$ (described herein with respect to FIGS. 6 and 7) are the same.

Target 66 may be fabricated in a different ways from a range of different materials. In one embodiment, annular body 90 is fabricated from aluminum that is anodized black. The patterns 120, 122, and 124 are then formed by etching, such as by laser etching, to remove the black anodization in the selected areas. The resultant ring-shaped patterns have sharp, crisp boundaries that are easy for machine vision techniques to detect.

FIG. 6 schematically shows a top view of a preferred deployment of machine vision cameras with respect to the docking target when the electron beam emitted by the electron beam treatment system of FIG. 1 is properly aimed at a treatment site. When the machine 16 is properly docked according to this configuration, each of the optical imaging devices overlies the target 66 in a manner such that the optical axis of each device 70 and 72 overlies and is aligned with the reference circle 126 on target 66. In this preferred mode of practice, each of devices 70 and 72 are arranged such that their optical axes are 90 degrees apart on circle 126 when the docking alignment is achieved. In this arrangement, each device 70 and 72 has one image axis in its captured image plane that is perpendicular to the tangent of the reference circle 126 on that one image axis. Along this one axis, the imaging capability of that device has its greatest sensitivity to relative translation of the target 66 relative to the device. Similarly, the imaging capability of that device has its greatest sensitivity to relative rotation of the target 66 about an axis in the image plane that is parallel to the plane of the rings and perpendicular to such image axis. Because the two devices 70 and 72 are clocked 90 degrees (orthogonally) to the target patterns, collectively the axes of great sensitivity of the two devices 70 and 72 are substantially orthogonal to each other. This complementary sensitivity provides a combined imaging capability that is sensitive to translation and rotation with respect to both main axes of the imaging plane. This allows the position and rotation of machine 16 relative to target 66 to be precisely determined and guided in three-dimensional space.

Figure 8:
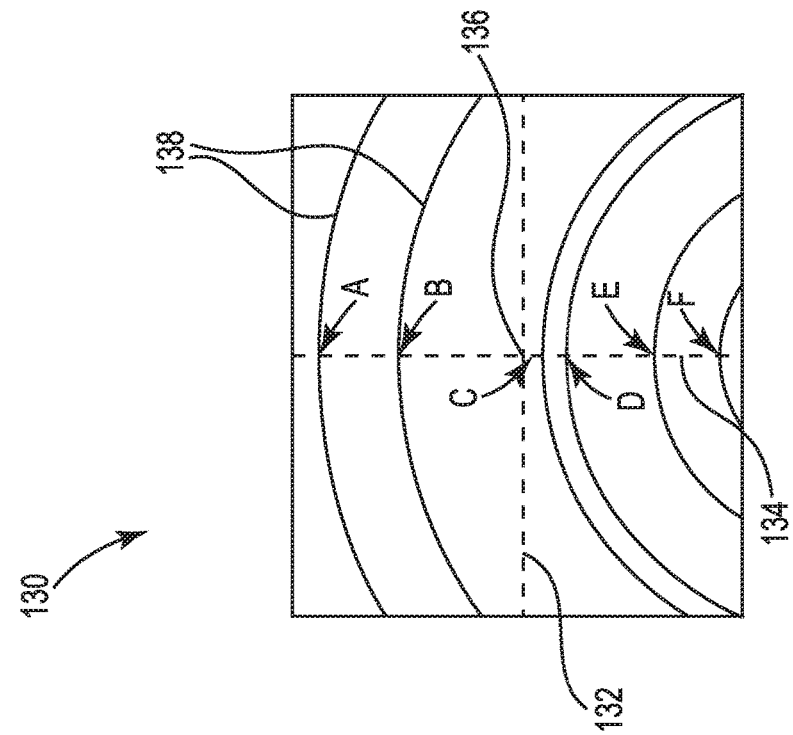
FIG. 8 schematically shows an illustrative processed image of the present invention including features whose locations in the image space correlate to the position and aim of the electron beam machine used in FIG. 1.

FIG. 8 schematically shows an illustrative processed image 130 of the present invention obtained from one of devices 70 or 72 observing target 66. Image 130 includes features whose locations in the image space correlate to the position and aim of the electron beam machine used in FIG. 1. Image 130 is obtained by appropriate processing (described further below with respect to FIGS. 17 and 18) of captured image information obtained by the device upon observation of target 66. The processed image 130 occupies an image space having horizontal axis 132 and vertical axis 134 that interest in the image space center 136. The captured image information is processed in order to extract locations of the boundaries or edges of the patterns 120, 122, and 124 on target 66. Techniques including erosion, smoothing, and dilation to remove small features as well as edge filters such as Canny algorithms may be used to produce a binary image that contains only the edge or boundary information of the observed patterns.

Using the process information, the intersections of the edge contours with one of the axes are determined. In the exemplary image 130, intersections of the vertical axis 134 with the edge contours are identified as points A, B, C, D, E, and F in the image space. The relationships among these points encode information about the relative position and orientation of the target 66 and electron beam machine 16. In particular, when $R_{camera}=R_{target}$, position and angular alignment information is easily derived from the processed image information. The location of the mid-point between points C and D relative to the image center 136 provides feedback about the disparity between the observing device's optical axis with respect to the reference circle 126. The distance between any two points in the image space provides information about the distance between the observing device and the target 66. Further, due to parallax principles, the fact that points C and D lie on a different plane than the other points A, B, E and F allows disparity between the apparent distances BC and DE in the image space to provide feedback about the angle between the observing device's optical axis and the normal vector of the target planes. Note that points A, B, C, D, E, and F are intersections between the edge contours and the horizontal axis 132 of the corresponding image space for one of the devices 70 and 72, but are the intersections between the edge contours and the vertical axis 134 of the corresponding image space for the other device.

As a result of these relationships, criteria for a properly docked configuration are easily specified. For example, the machine 16 can be said to be properly docked when the following conditions are met simultaneously by the image information acquired by both of devices 70 and 72:

1. The midpoint of CD is coincident with the center 136 of each device's image plane (i.e., the optical axis of each device 70 and 72 is aligned with the reference circle 126);
2. The midpoint of CD is coincident with the midpoint of BE in the image space for each device; and
3. The length of BE in the image space matches a predetermined length predetermined by calibration.

In an exemplary mode of using machine vision control to guide machine 16 into a proper docking configuration with applicator assembly 22, controller 28 generates error signals based on measured deviations from these docking conditions in order to generate control signals. Via closed loop feedback control, the controller 28 sends control signals to one or more actuation devices 30 to cause corrective translation or rotation of the devices 70 and/or 72 as appropriate so as to minimize these errors and achieve the desired docking configuration within acceptable tolerances. Preferably, the optical axes of the devices 70 and 72 are substantially parallel to the electron beam axis 20 so that alignment of the optical axes of the devices 70 and 72 to the target 66 also results in alignment of electron beam axis 20 to applicator axis 26 within acceptable tolerances to align properly docked radiation treatment.

Figure 9B:
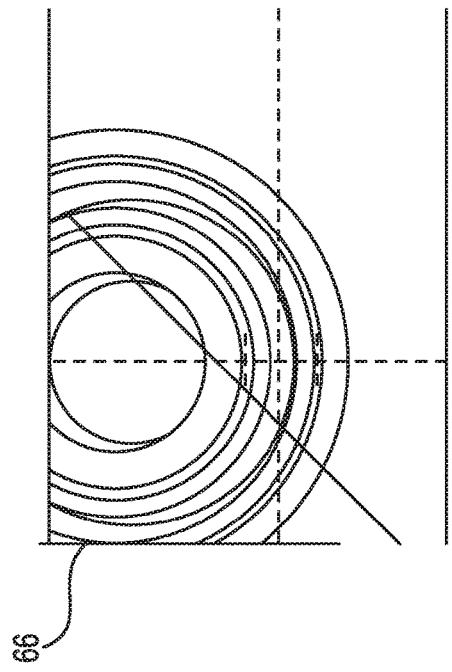
FIG. 9*b* is a schematic view of the image of the docking target acquired by the first image capture device of FIG. 9*a*.
Figure 9C:
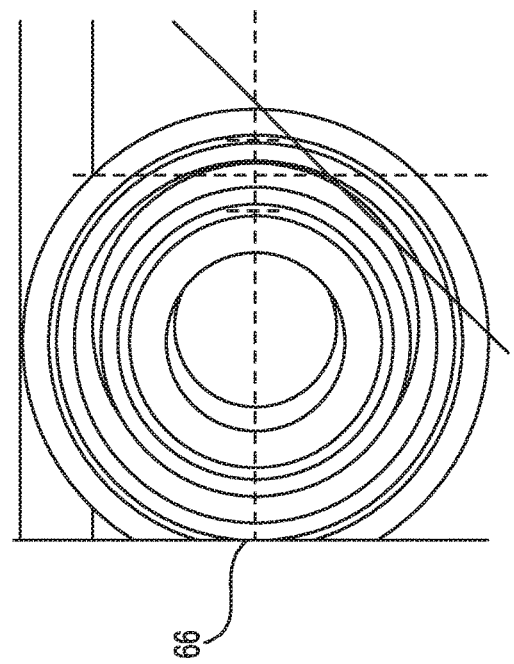
FIG. 9*c* is a schematic view of the image of the docking target acquired by the second image capture device of FIG. 9*a*.
Figure 9A:
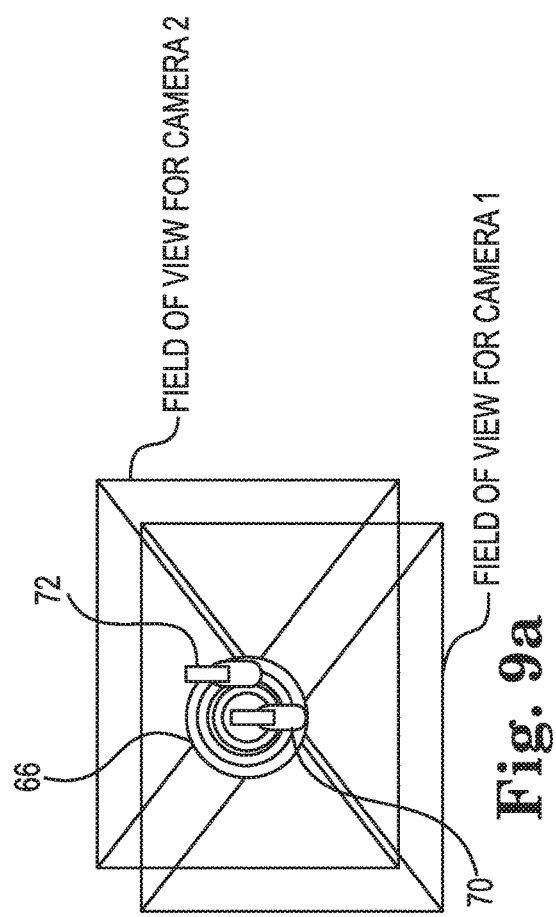
FIG. 9*a* is a top view schematically showing how first and second image capturing devices of the system of FIG. 1 are aligned with the docking target when the electron beam machine is properly positioned and aimed.

FIG. 9a is a top view schematically showing how first and second image capturing devices 70 and 72 of the system 10 of FIG. 1 are aligned with the docking target 66 when the electron beam machine 16 is in a desired docking configuration. The optical axis of each device 70 and 72 is aligned with the reference circle 126. Corresponding images captured by devices 70 and 72 in this docked configuration are shown in FIGS. 9b and 9c. Device 70 examines intersections of the pattern contours with the vertical axis of the image space, while device 72 examines intersections of the pattern contours with the horizontal axis of the image space. In both images along the axis under evaluation, the middle ring pattern is centered between the inner and outer ring patterns. Also, the center of the middle ring is located at the center of the image space. Further, the distance between the inner and outer patterns match the desired calibrated distance, conveniently expressed as image pixels.

Figure 10B:
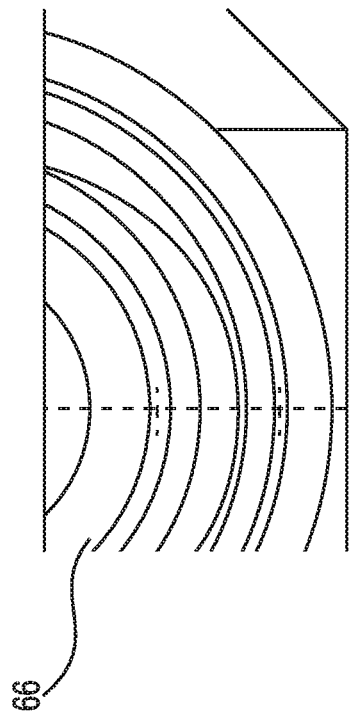
FIG. 10*b* is a schematic view of the image of the docking target acquired by the first image capture device of FIG. 10*a*.
Figure 10C:
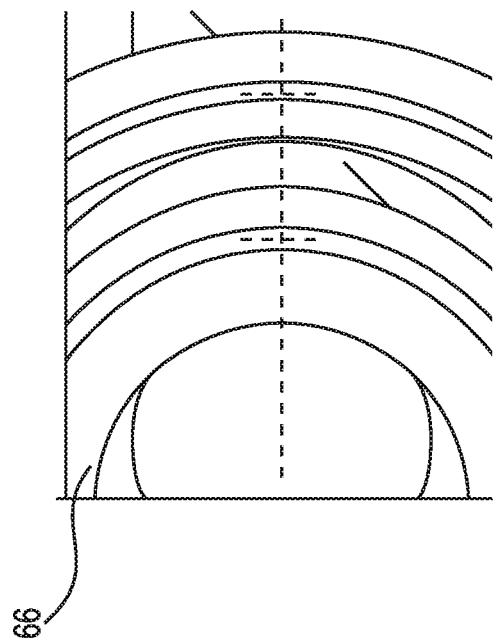
FIG. 10*c* is a schematic view of the image of the docking target acquired by the second image capture device of FIG. 10*a*.
Figure 10A:
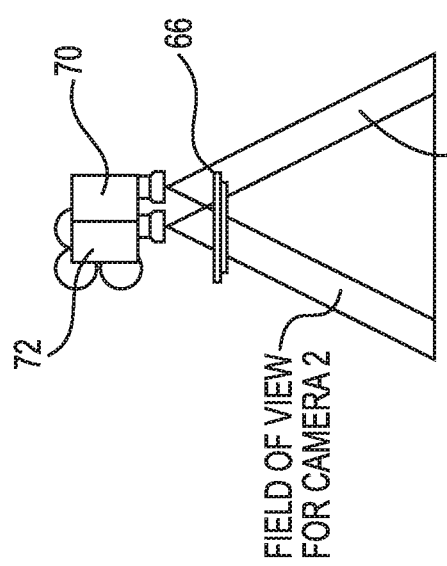
FIG. 10*a* is a side view schematically showing how first and second image capturing devices and electron beam of the system of FIG. 1 are properly aligned with the docking target but the devices are positioned too close in distance.
Figure 11B:
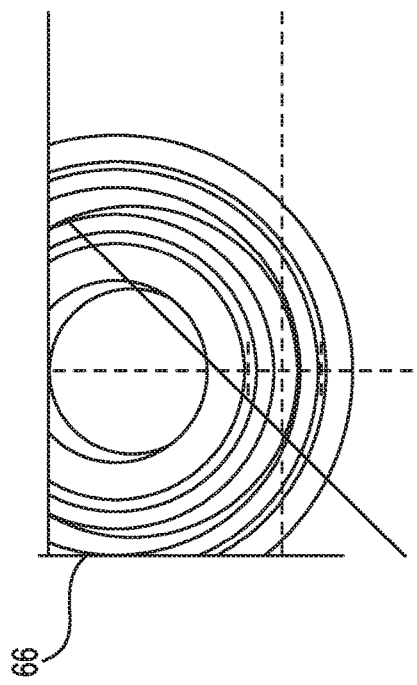
FIG. 11*b* is a schematic view of the image of the docking target acquired by the first image capture device of FIG. 12*a*.
Figure 11C:
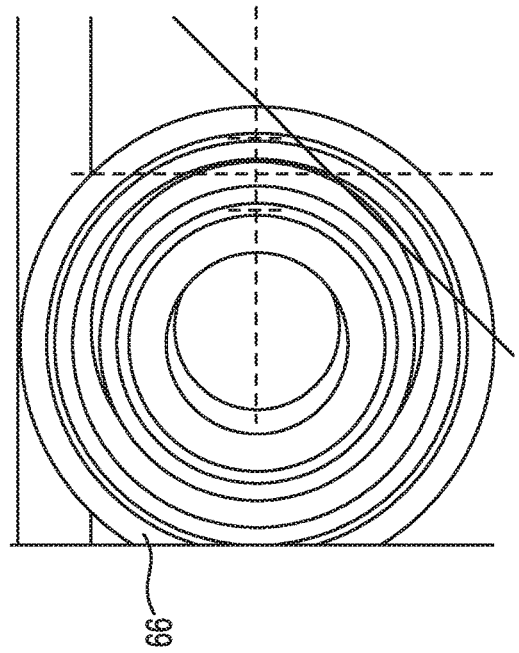

FIG. 10a is a side view schematically showing how first and second image capturing devices 70 and 72 and electron beam axis 20 of the system 10 of FIG. 1 are properly aligned with the docking target 66, but the devices 70 and 72, and hence machine 16, are positioned too close in distance to the target 66. Corresponding images captured by devices 70 and 72 in this configuration are shown in FIGS. 11b and 11c. Device 70 examines intersections of the pattern contours with the vertical axis of the image space, while device 72 examines intersections of the pattern contours with the horizontal axis of the image space. In both images along the axis under evaluation, the middle ring pattern is centered between the inner and outer ring patterns. Also, the center of the middle ring is located at the center of the image space. This information indicates that the optical axes of the devices 70 and 72 and the electron beam axis 20 are aligned with the applicator axis 26. However, in each image space, the distance between the inner and outer patterns is smaller than the desired calibrated distance, conveniently expressed as image pixels.

Figure 11A:
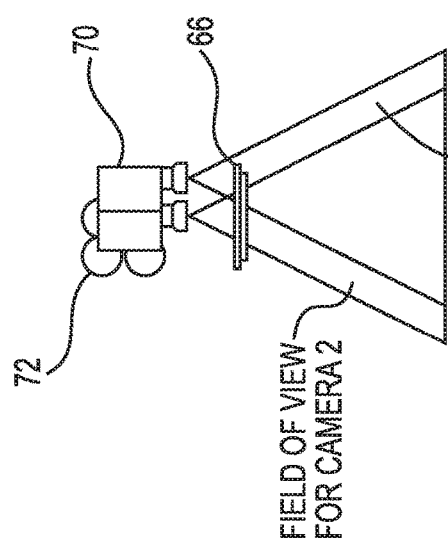
FIG. 11*a* is a side view schematically showing how first and second image capturing devices and electron beam axis of the system of FIG. 1 are aligned with the docking target but is positioned too far from the docking target in distance.

FIG. 11a is a side view schematically showing how first and second image capturing devices 70 and 72 and electron beam axis 20 of the system 10 of FIG. 1 are properly aligned with the docking target 66, but the devices 70 and 72, and hence machine 16, are positioned too far in distance from the target 66. Corresponding images captured by devices 70 and 72 in this configuration are shown in FIGS. 11b and 11c. Device 70 examines intersections of the pattern contours with the vertical axis of the image space, while device 72 examines intersections of the pattern contours with the horizontal axis of the image space. In both images along the axis under evaluation, the middle ring pattern is centered between the inner and outer ring patterns. Also, the center of the middle ring is located at the center of the image space. This information indicates that the optical axes of the devices 70 and 72 and the electron beam axis 20 are aligned with the applicator axis 26. However, in each image space, the distance between the inner and outer patterns is larger than the desired calibrated distance, conveniently expressed as image pixels.

Figure 12B:
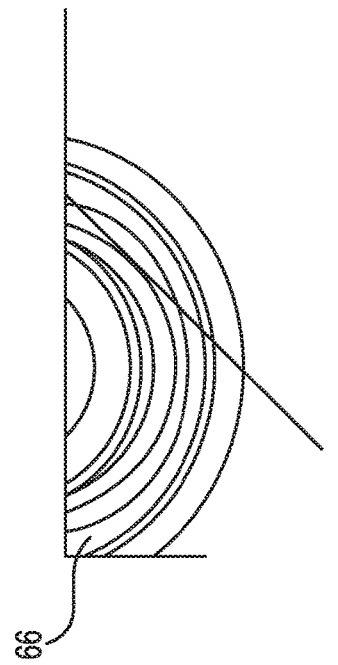
Figure 12C:
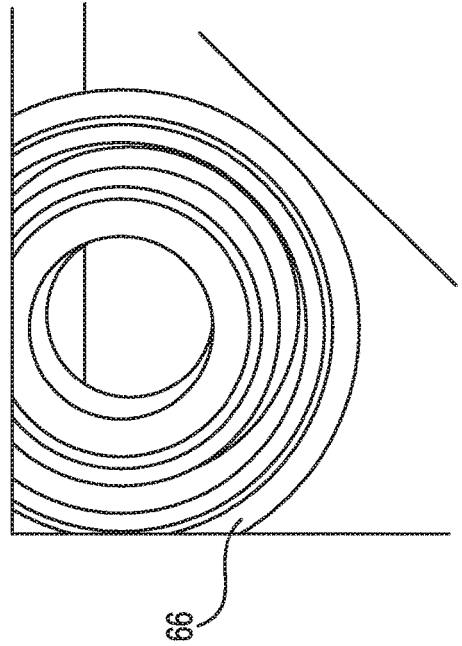
Figure 12A:
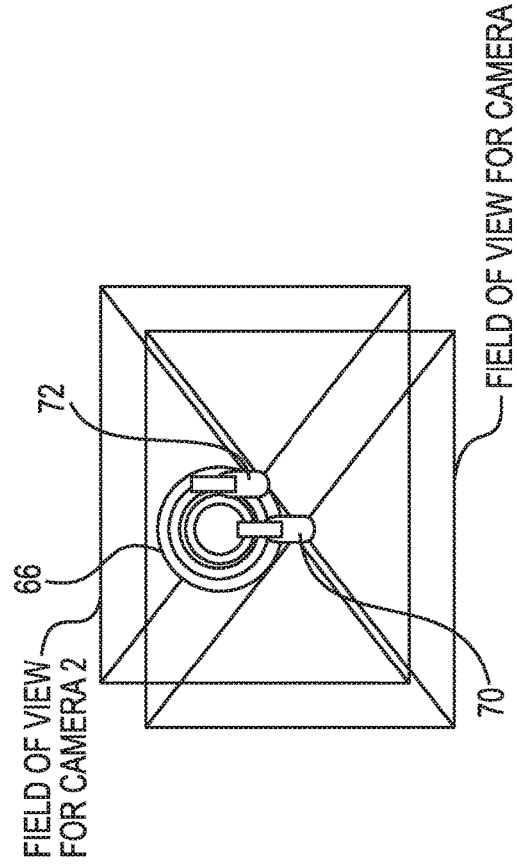
FIG. 12a is a top view schematically showing how first and second image capturing devices, and hence the electron beam axis, of the system of FIG. 1 are parallel with the docking target and are at a proper distance from the docking target along the z-axis (perpendicular to the plane of the docking target), but both the devices, and hence the electron beam axis are shifted out of alignment in the y-axis.

FIG. 12a is a top view schematically showing how first and second image capturing devices 70 and 72, and hence the electron beam axis 20, of the system 10 of FIG. 1 are aligned parallel with the docking target 66 and are at a proper distance from the docking target 66 along the z-axis), but both the devices 70 and 72, and hence the electron beam axis 20, are shifted out of alignment in the y-axis. Corresponding images captured by devices 70 and 72 in this docked configuration are shown in FIGS. 12b and 12c. Device 70 examines intersections of the pattern contours with the vertical axis of the image space, while device 72 examines intersections of the pattern contours with the horizontal axis of the image space. The image captured by device 70 exhibits a displacement of the middle ring relative to the inner and outer rings due to parallax effects. The vertical position of the middle ring in the image plane also is shifted in a manner that is proportional to the displacement. The image captured by device 72 also exhibits distortion due to parallax effects. However, because the translation error is substantially parallel to the device's view of the displacement, the sensitivity of device 72 to the displacement error is less than that of device 70.

Figure 13B:
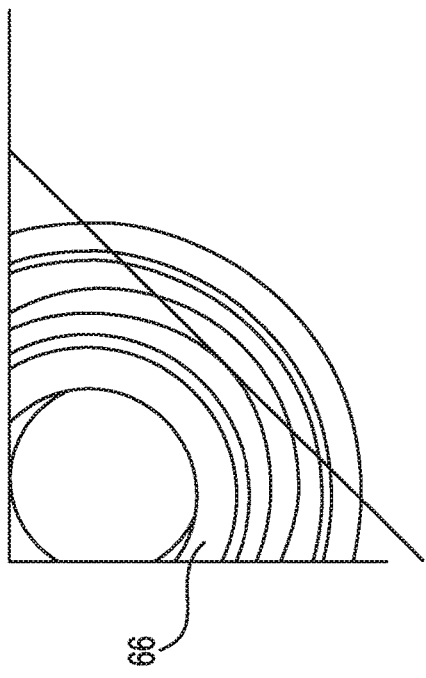
Figure 13C:
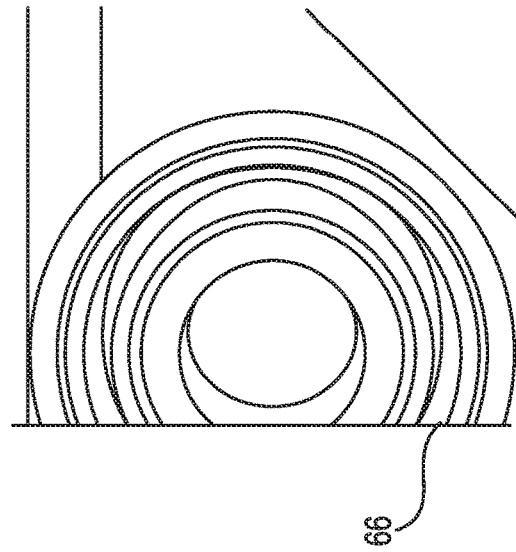
Figure 13A:
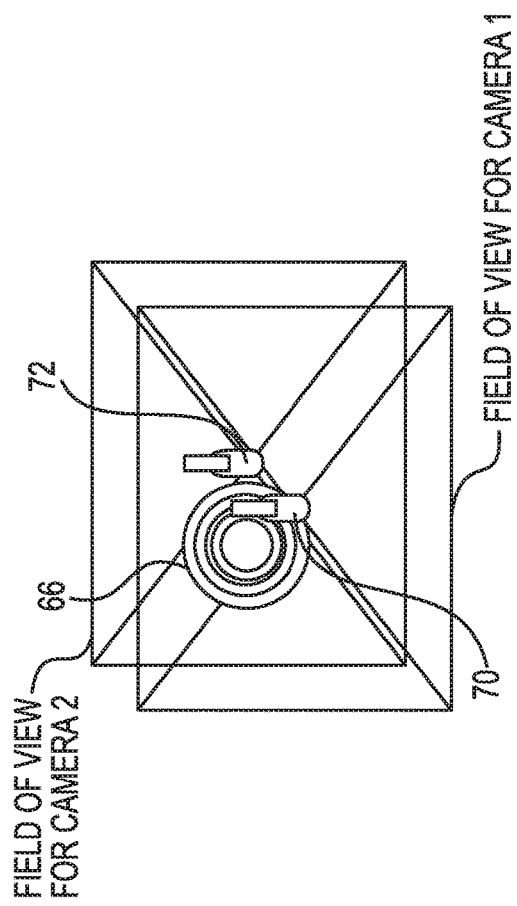
FIG. 13a is a top view schematically showing how first and second image capturing devices, and hence the electron beam axis, of the system of FIG. 1 are parallel with the docking target and are at a proper distance from the docking target along the z-axis (perpendicular to the plane of the docking target), but both the devices, and hence the electron beam axis are shifted out of alignment in the x-axis.

FIG. 13*a* is a top view schematically showing how first and second image capturing devices, and hence the electron beam axis, of the system of FIG. 1 are parallel with the docking target and are at a proper distance from the docking target along the z-axis (perpendicular to the plane of the docking target), but both the devices, and hence the electron beam axis are shifted out of alignment in the x-axis. Corresponding images captured by devices 70 and 72 in this docked configuration are shown in FIGS. 13*b* and 13*c*. Device 70 examines intersections of the pattern contours with the vertical axis of the image space, while device 72 examines intersections of the pattern contours with the horizontal axis of the image space. The image captured by device 72 exhibits a displacement of the middle ring relative to the inner and outer rings due to parallax effects. The horizontal position of the middle ring in the image plane also is shifted in a manner that is proportional to the displacement. The image captured by device 70 also exhibits distortion due to parallax effects. However, because the translation error is substantially parallel to the device's view of the displacement, the sensitivity of device 70 to the displacement error is less than that of device 72.

Figure 14B:
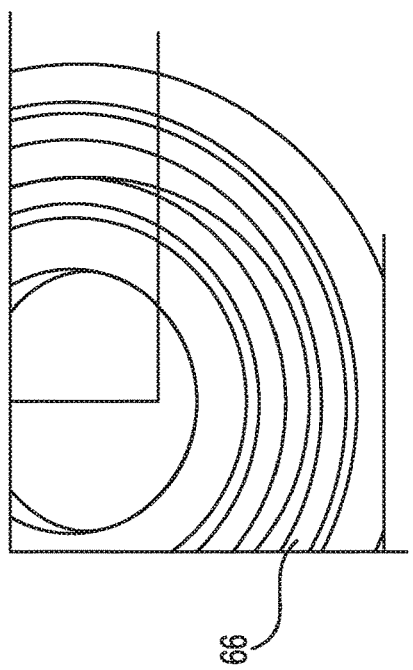
Figure 14C:
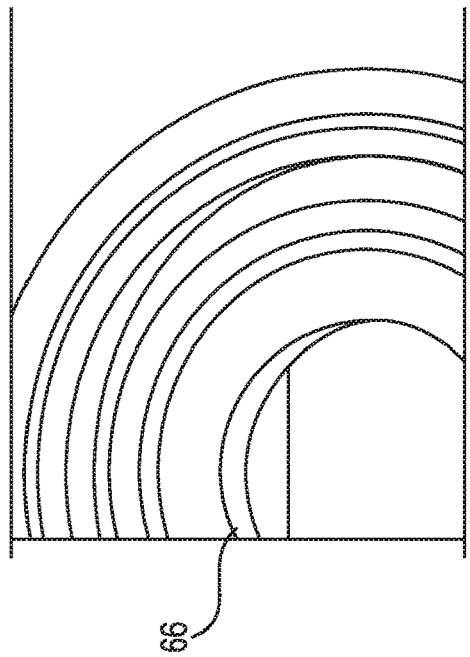
Figure 14A:
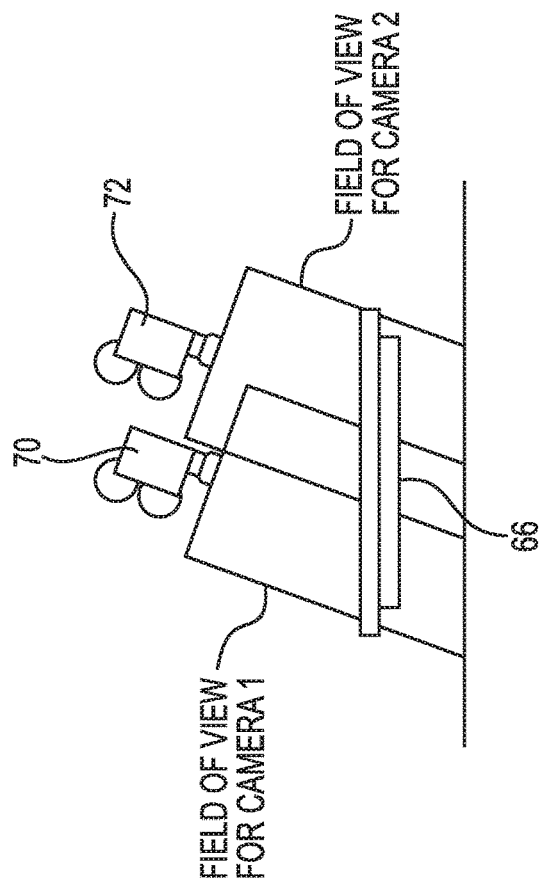
FIG. 14a is a side view along the x-axis schematically showing how first and second image capturing devices, and hence the electron beam axis, of the system of FIG. 1 are shifted out of alignment with the docking target by rotation of the devices, and hence the electron beam axis, about the x-axis.

FIG. 14*a* is a side view along the x-axis schematically showing how first and second image capturing devices 70 and 72, and hence the electron beam axis 20, of the system 10 of FIG. 1 are shifted out of alignment with target 66 by rotation of the devices 70 and 72, and hence the electron beam axis 20, about the x-axis. Corresponding images captured by devices 70 and 72 in this docked configuration are shown in FIGS. 14*b* and 14*c*. Device 70 examines intersections of the pattern contours with the vertical axis of the image space, while device 72 examines intersections of the pattern contours with the horizontal axis of the image space. Device 70 is most sensitive to this rotation. In its image, the rotation causes more displacement of the center ring relative to the inner and outer rings. The vertical position of the center ring observed by device 70 also shows greater displacement.

FIG. 15*a* is a side view along the y-axis schematically showing how first and second image capturing devices 70 and 72, and hence electron beam axis 20, of the system 10 of FIG. 1 are shifted out of alignment with the docking target 66 by rotation of the devices 70 and 72, and hence the electron beam axis 20, about the y-axis. Corresponding images captured by devices 70 and 72 in this docked configuration are shown in FIGS. 15*b* and 15*c*. Device 70 examines intersections of the pattern contours with the vertical axis of the image space, while device 72 examines intersections of the pattern contours with the horizontal axis of the image space. Device 72 is most sensitive to this rotation. In its image, the rotation causes more displacement of the center ring relative to the inner and outer rings. The horizontal position of the center ring observed by device 72 also shows greater displacement.

Figure 16:
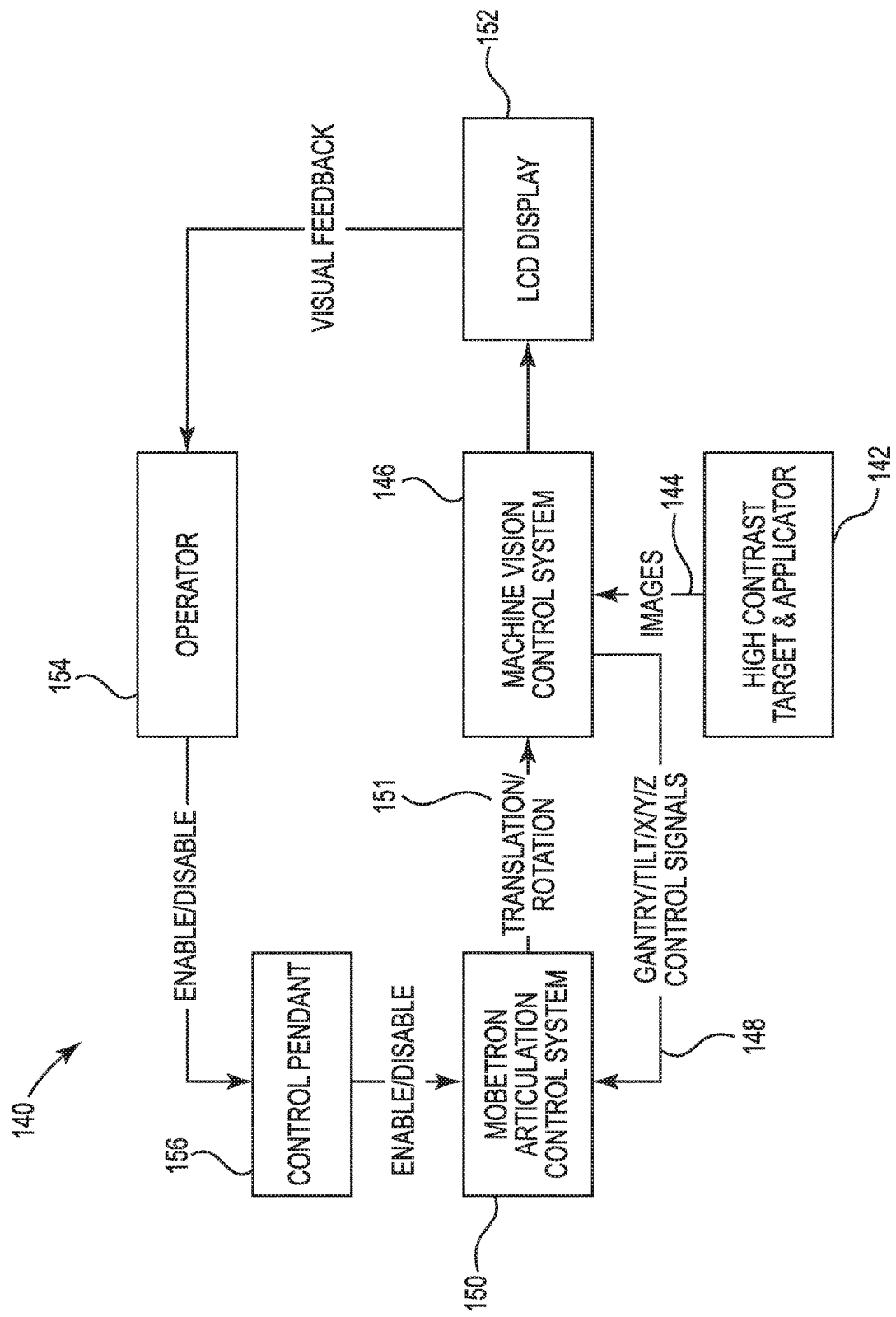
FIG. 16 schematically shows how machine vision functionality is incorporated into the electron beam treatment system of FIG. 1.

FIG. 16 schematically shows an exemplary methodology 140 of practicing machine vision functionality in the electron beam treatment system 10 of FIG. 1. In step 142, image capturing device 70 and 72 capture image information of the docking target 66. The captured image information is provided to controller 28 via pathway 144. In step 146, controller 28 uses the captured image information to generate translation and/or rotation control signals that are based on differences between the sensed position of the devices 70 and 72 and the desired positions when a proper docking configuration is achieved. Controller 28 then transmits appropriate control signals to the actuation devices 30 along pathway 148 that are intended to cause translation or rotation of the devise 70 and 72, and hence of the electron beam machine 16, into the desired docking configuration. Confirmation of the change in translation or rotation is sent to the controller 28 so that the controller 28 is aware that translation and/or rotation occurred.

Methodology 140 also provides an interface between the machine vision control methodology and one or more system operators. In step 152, controller 28 outputs information to a suitable display or other operator interface so that the operator can follow, evaluate or otherwise observe the progress of the machine vision docking procedure. The operator is able to interact with the system at step 154 via this interface. The operator is able to input information, instructions or otherwise interact with the methodology via step 156.

Figure 17:
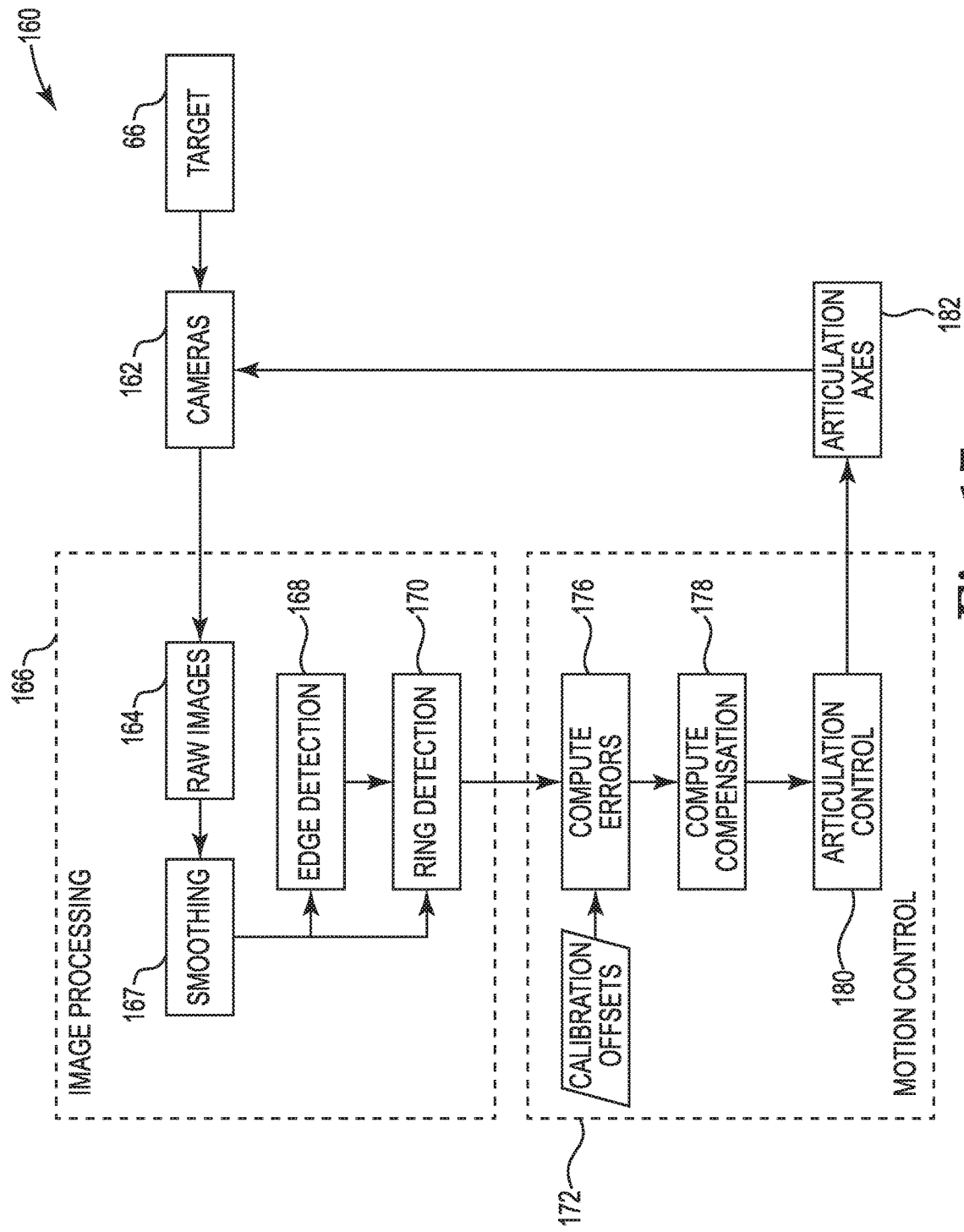
FIG. 17 is a flow diagram that schematically shows how machine vision guidance acquires and processes image information in order to implement automatic docking procedures.

FIG. 17 is a flow diagram that schematically shows how machine vision guidance implements an illustrative methodology 160 that acquires and processes image information in order to implement automatic docking procedures. In step 162, the image capture devices 70 and 72 capture image information of the target 66. The devices 70 and 72 are rigidly coupled to the machine 16 in a manner such that the optical axes of the devices 70 and 72 are substantially parallel to the electron beam axis 20 and such that the image planes are substantially perpendicular to the electron beam axis 20. Consequently, translation and rotation of the devices 70 and 72 results in a matched translation and rotation of the electron beam axis 20.

In step 164, the captured image information is transmitted to controller 28. In an image processing phase 166, controller 28 processes the image so that position and angular alignment information encoded in the image data can be evaluated. In step 166, an exemplary processing includes smoothing of the image data. In step 168, edge detection is performed to identify the edge contours of the patterns on the target 66. In step 170, ring detection is performed in order to determine how the edge contours intersect the axis or axes of the image space.

With the images processed, a next phase 172 uses the processed image information to implement motion control. In step 176, the processed image information is compared to reference data comprising calibration information. Using disparities between the processed image information and the calibration information, step 176 computes rotation and/or translation errors. In step 178, compensations to correct the errors are generated. In step 180, the control signals cause appropriate articulation signals to be sent to machine 16. In step 182, the machine 16 translates and/or rotates responsive to the control signals. Then, the cycle repeats by capturing more image information in step 162.

Optionally, preferred modes of carrying out machine vision functionality with respect to system 10 of FIG. 1 may involve monitoring system 10 and implementing an interlock functionality when appropriate. For example, an interlock signal can disable or otherwise attenuate the electron beam during a treatment if evaluation of captured image information indicates that the machine 16 is not in the desired docking configuration within acceptable tolerances. The interlock functionality may be practiced in real-time with respiratory gating in order to disable or modulate the electron beam in the event that respiration of the patient causes the machine 16 to repeatedly move in and out of the desired docking configuration.

For example, the docking system may provide an interlock signal to prevent application of the electron beam until the treatment head and the applicator are correctly aligned. Once the desired position and alignment are achieved, the docking system may monitor position and alignment during the course of a treatment. The system can implement corrections (e.g., beam interlock or corrections to alignment and position) in response to position information derived from observing the docking target. In the event that respiration or other movement of the patient causes the docking configuration to be lost, the system could generate a signal that disables the electron beam until the desired configuration is achieved again. Alternatively, the logic of the interlock or gating programming could require a signal level from the docking system in order to produce an electron beam. In the absence of such a signal, the beam would be disabled unless and until the signal were to be reestablished. Such gating of machine function as a consequence of respiration may occur repeatedly during the course of a treatment. Real-time gating and interlock can be practiced because the system can monitor and implement docking and/or interlock corrections so rapidly. In contrast to the simple and fast, real-time respiratory and gating functions allowed by the present invention, this kind of functionality is more difficult to achieve using conventional docking approaches due to the time it takes in such systems to assess alignment in the first instance and then to take action upon an assessment.

Implementing interlock or gate functionality may involve control of electron beam sources. Electron beam sources are typically diode-type or triode-type electron guns, with a high-voltage applied between cathode and anode, either DC or pulsed, and, in the case of the triode-type gun, a lower grid voltage applied between the cathode and grid. The grid can disable or enable beam, and the grid voltage may be varied continuously to inject more or less gun current. For the diode gun beam-inhibit is also possible, by refraining from pulsing of the gun.

Due to the ability of the present invention to rapidly and accurately respond and implement docking information in real time, the present invention can be used to accomplish patient motion management, such as respiratory gating, circulatory gating, or gating on episodic movements such as in the gastrointestinal system. Respiratory gating enables and disables the electron beam to accommodate patient motion in the event that respiration or other movement of the patient causes the treatment machine to move into and out of a desired docking configuration. Respiratory gating, therefore, generally includes inhibiting the beam when docking variables (e.g., angle, position) fall outside the desired tolerances. In the simplest implementation this, a beam-inhibit correction could thereafter require manual intervention to reset an interlock and continue treatment. More preferably, a beam inhibit would not require manual intervention to restart treatment. Rather, beam inhibit could be followed, e.g., after a brief period such as a few seconds of beam inhibit, followed by recovery of docking variable values within the tolerable range. In the case of rhythmic patient motion, such as respiratory or circulatory motion, the corresponding rhythmic pattern of beam-on, beam-inhibit would ensure more accurate treatment of the intended planning target volume. In addition to gating, the present invention enables automated recovery of the docking condition, and active tracking to avoid loss of the docking condition. The docking system adjusts and re-docks or maintains docking within tolerances, when the patient movement results or would result in beam-inhibit.

The embodiments of the present invention described herein are not intended to be exhaustive or to limit the invention to the precise forms disclosed in the specification and Figures. Rather a purpose of the illustrative embodiments chosen and described is so that the appreciation and understanding by others skilled in the art of the principles and practices of the present invention can be facilitated. While illustrative embodiments of the present invention have been shown and described herein, the skilled worker will appreciate that such embodiments are provided by way of example and illustration only. Numerous variations, changes, and substitutions will now occur to those skilled in the art without departing from the invention. No unnecessary limitations are to be understood therefrom. The invention is not limited to the exact details shown and described, and any variations are included that are within the scope of the claims.

All patents, patent applications, and publications cited herein are incorporated by reference in their respective entireties for all purposes.

What is claimed is:

1. An electron beam treatment system that automatically aims an electron beam with respect to a treatment site, said system comprising:
    a) an electron beam machine that emits an electron beam on an electron beam path;
    b) an applicator located with respect to the treatment site such that the electron beam is aimed at the treatment site through the applicator when the electron beam is properly aligned, said applicator having an applicator axis; and
    c) a machine vision system that automatically positions the electron beam machine at a position and angular alignment relative to the applicator to aim the electron beam through the applicator at the treatment site, said machine vision system comprising:
        i. a docking target coupled to the applicator and comprising a plurality of concentric facets having a common optical axis that is aligned with the applicator axis, wherein said common optical axis is aligned with the electron beam path when the electron beam is properly aimed at the treatment site, wherein the plurality of concentric facets comprise at least first and second facets, wherein at least one of the first and second facets of the docking target comprises imageable characteristics that encode a parallax disparity relative to reference image information that is indicative of an aim misalignment when the electron beam is improperly aimed at the treatment site, and wherein the imageable characteristics of at least one of the first and second facets encode a distance disparity relative to reference image information that is indicative of a distance error when the electron beam machine is at a distance from the docking target that is different from a desired distance,
        ii. first and second image capturing devices coupled to the electron beam machine in a manner effective such that each image capturing device observes and captures image information of the docking target from first and second observation perspectives, respectively, wherein at least first and second facets of the docking target are characterized by at least one of a different distance or a different angle of presentation with respect to the observation perspectives, and wherein the captured image information encodes information indicative of the alignment and distance of the electron beam machine relative to the applicator, and iii. a machine vision control system comprising program instructions that use the image information captured by the first and second image capturing devices to position the electron beam machine into a desired alignment and distance relative to a target in order to aim the electron beam at the treatment site.

2. The electron beam treatment system of claim 1, wherein the electron beam has an axis, and wherein the electron beam is aimed through the applicator at the treatment site when the electron beam axis and the applicator axis are parallel and co-linear.

3. The electron beam treatment system of claim 1, wherein the electron beam is a linearly accelerated, straight through electron beam.

4. The electron beam treatment system of claim 1, wherein the electron beam machine comprises a collimator that broadens and flattens the electron beam.

5. The electron beam treatment system of claim 1, wherein the image information encodes information indicative of the distance and angular alignment of the electron beam machine with respect to the docking target.

6. The electron beam treatment system of claim 1, wherein the first and second image capturing devices are orthogonally deployed to provide distance and angular alignment sensitivity on two different, orthogonal image plane axes.

7. The electron beam treatment system of claim 1, wherein each of the first and second image capturing devices observe the docking target from an observation origin, wherein the electron beam has an electron beam axis, and wherein the observation origins are equidistant from the electron beam axis.

8. The electron beam treatment system of claim 1, wherein the first facet comprises a first detectable edge boundary that comprises edge information of an observed first pattern on the docking target.

9. The electron beam treatment system of claim 8, wherein the second facet comprises a second detectable edge boundary that comprises edge information of an observed second pattern on the docking target.

10. The electron beam treatment system of claim 1, wherein the first facet comprises a first imageable pattern and the second facet comprises a second imageable pattern, and wherein the first and second imageable patterns are annular and concentric.

11. The electron beam treatment system of claim 1, wherein the docking target comprises an annular body.

12. The electron beam treatment system of claim 1, wherein the first and second facets are rotational symmetric.

13. The electron beam treatment system of claim 1, wherein the first facet comprises a first imageable pattern and the second facet comprises a second imageable pattern, and wherein each of the first and second imageable patterns comprises a unique distance and angle presentation with respect to the first and second image capturing devices.

14. The electron beam treatment system of claim 1, wherein the first and second facets are annular, concentric, and coplanar.

15. The electron beam treatment system of claim 1, wherein the first facet is on a first plane, the second facet is on a second, different plane, and the first and second planes are parallel.

16. The electron beam treatment system of claim 1, wherein the first and second facets comprise surfaces with a matte finish.

17. The electron beam treatment system of claim 1, wherein the docking target comprises aluminum.

18. The electron beam treatment system of claim 1, wherein the docking target comprises anodized aluminum.

19. The electron beam treatment system of claim 18, wherein selected areas of the anodized aluminum are removed to form an imageable pattern on each of the first and second facets.

20. The electron beam treatment system of claim 1, wherein the parallax disparity includes parallax effects that can be used to increase sensitivity of observations to both translational and rotational disparity from the desired position and angular alignment of the electron beam relative to the treatment site.

21. A method of positioning and aligning a first object with a second object, comprising the steps of:
a) locating a docking target with respect to the first object, wherein the docking target comprises a plurality of concentric facets having a common optical axis, wherein at least first and second facets comprise first and second imageable characteristics, respectively, wherein at least one of the first and second imageable characteristics encodes a parallax disparity when the docking target is viewed from a perspective that is different from a desired perspective, and wherein at least one of the first and second imageable characteristics encodes a distance disparity when a target is viewed from a perspective that is at a different distance from the docking target than a desired distance;
b) locating first and second image capturing devices with respect to the second object;
c) using the located first and second image capturing devices to observe and capture image information of the target from first and second perspectives, respectively; and
d) using the captured image information to guide the first object into a desired position and angular alignment relative to the second object.

22. A method of aiming an electron beam at a treatment site, comprising the steps of:
a) providing an electron beam machine that emits an electron beam on an electron beam path;
b) providing an applicator located with respect to the treatment site such that the electron beam is aimed at the treatment site through the applicator when the electron beam is properly aligned, said applicator having an applicator axis;
c) locating a docking target with respect to the applicator, wherein the docking target comprises a plurality of concentric facets having a common optical axis, wherein at least first and second facets comprise first and second imageable characteristics, respectively, wherein at least one of the first and second imageable characteristics imageable characteristics encode a parallax disparity relative to reference image information that is indicative of an aim misalignment when the electron beam is improperly aimed at the treatment site, and wherein the imageable characteristics of at least one of the first and second facets encode a distance disparity relative to reference image information that is indicative of a distance error when the electron beam machine is at a distance from the docking target that is different from a desired distance;

d) providing first and second image capturing devices coupled to the electron beam machine in a manner effective such that each image capturing device observes and captures image information of the docking target from first and second perspectives, respectively, wherein the captured image information encodes information indicative of the alignment and distance of the electron beam machine relative to the applicator; and e) using the image information captured by the first and second image capturing devices to position the electron beam machine into a desired alignment and distance relative to a target in order to aim the electron beam at the treatment site.

23. A method of using an electron beam to treat a patient, comprising the steps of:
a) docking the electron beam system of claim 1 into a desired docking configuration with the patient; and
b) while the electron beam system of claim 1 is in the desired docking configuration, using the electron beam system to irradiate a treatment site on the patient with an electron beam.

24. A method of using an electron beam to treat a patent, comprising the steps of:
a) docking the electron beam system of claim 1 into a desired docking configuration with the patient;
b) while the electron beam system of claim 1 is in the desired docking configuration, using the electron beam system to irradiate a treatment site on the patient with an electron beam;
c) during step (b), monitoring information indicative of whether the electron beam system is in the desired docking configuration; and
d) using the monitored information to disable the electron beam when the monitored information indicates that the electron beam system is not in the desired docking configuration.

25. A method of using an electron beam to treat a patent, comprising the steps of:
a) docking the electron beam system of claim 1 into a desired docking configuration with the patient;
b) while the electron beam system of claim 1 is in the desired docking configuration, using the electron beam system to irradiate a treatment site on the patient with an electron beam;
c) during step (b), observing the docking target to capture image information of the docking target;
d) during step (b), using the image information in real time to provide signal information indicative of whether the electron beam system is in the desired docking configuration; and
e) using the signal information to disable the electron beam when the signal information indicates that the electron beam system is not in the desired docking configuration.

* * * * *